United States Patent [19]

Schmidlin et al.

[11] Patent Number: 5,369,110
[45] Date of Patent: Nov. 29, 1994

[54] BIPHENYLYL COMPOUNDS

[75] Inventors: Tibur Schmidlin, Basel; Franz Ostermayer, Riehen; Peter Bühlmayer, Arlesheim, all of Switzerland

[73] Assignee: Ciba-Geigy Corporation, Ardsley, N.Y.

[21] Appl. No.: 89,393

[22] Filed: Jul. 9, 1993

Related U.S. Application Data

[63] Continuation of Ser. No. 805,256, Dec. 9, 1991, abandoned.

[30] Foreign Application Priority Data

Dec. 14, 1990 [CH] Switzerland .................. 03965/90

[51] Int. Cl.$^5$ .................. A61K 31/41; C07D 257/04
[52] U.S. Cl. .................................. 514/281; 548/253
[58] Field of Search .................. 548/253; 514/281

[56] References Cited

FOREIGN PATENT DOCUMENTS

| 2014008 | 10/1990 | Canada | 548/253 |
| 425921 | 5/1991 | European Pat. Off. | 548/253 |
| 426021 | 5/1991 | European Pat. Off. | 548/253 |
| 443983 | 8/1991 | European Pat. Off. | 514/281 |
| 2677016 | 5/1991 | France | 548/253 |

OTHER PUBLICATIONS

CA 116(15):151772t Preparation of ... antagonists, Buehlmayer et al., p. 882, 1992.
CA115(13):136102k Preparation ... antagonists, Oku et al. p. 984, 1991.
CA115(15):159142n Preparation ... antagonists, Naka et al. p. 941, 1991.
European Search Report dated Sep. 8, 1992.

*Primary Examiner*—Johann Richter
*Assistant Examiner*—Joseph K. McKane
*Attorney, Agent, or Firm*—Irving M. Fishman; Karen G. Kaiser

[57] ABSTRACT

Biphenylyl compounds of formula

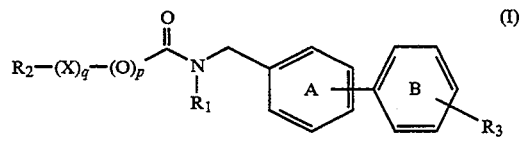

wherein the variables $R_1$, $R_2$, $R_3$, p, q and X and the rings A and B are as defined in claim 1, in free form or in salt form, can be prepared in a manner known per se and can be used, for example, as active ingredients in medicaments.

14 Claims, No Drawings

BIPHENYLYL COMPOUNDS

This application is a continuation of application Ser. No. 07/805,256, filed Dec. 9, 1991 now abandoned.

The invention relates to biphenylyl compounds of formula

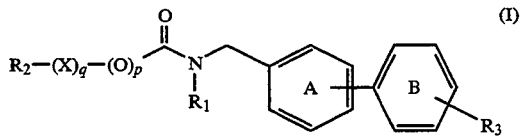

wherein $R_1$ is an aliphatic hydrocarbon radical that is unsubstituted or is substituted, in a position higher than the β-position with respect to the nitrogen atom shown in formula I, by halogen or by hydroxy, or is a cycloaliphatic hydrocarbon radical or an araliphatic hydrocarbon radical; $R_2$ is 1H-tetrazol-5-yl, carboxy, esterified carboxy, amidated carboxy, amino, substituted amino, acylamino, formyl, acetalised formyl, hydroxy, etherified hydroxy, $S(O)_m$—R, wherein m is 0, 1 or 2 and R is hydrogen or an aliphatic hydrocarbon radical, or alkanoyl, aminosulfonyl, N-substituted aminosulfonyl, $PO_2H_2$, $PO_3H_2$ or S-substituted sulfonylamino; $R_3$ is carboxy, 1H-tetrazol-5-yl, $SO_3H$, $PO_2H_2$, $PO_3H_2$ or haloalkanesulfonylamino; X is straight-chained alkylene that may be aliphatically bridged and/or that is unsubstituted or is substituted by an aliphatic hydrocarbon radical, or is the structural element of the formula —$X_1$—Ph—$X_2$—, wherein each of $X_1$ and $X_2$, independently of the other, is a bond or alkylene and Ph is unsubstituted or substituted phenylene; each of the rings A and B, independently of the other, is unsubstituted or is substituted by halogen, hydroxy, etherified hydroxy, $S(O)_m$—R, wherein m is 0, 1 or 2 and R is hydrogen or an aliphatic hydrocarbon radical, or by an aliphatic hydrocarbon radical that may be interrupted by O and/or that is unsubstituted or is substituted by halogen or by hydroxy, and either p and q are both 1 or p is 0 and q is 0 or 1; in free form or in salt form; to the use of those compounds, to a process for the preparation of those compounds and to pharmaceutical compositions that contain such a compound I in free form or in the form of a pharmaceutically acceptable salt.

The compounds I may be in the form of salts, especially pharmaceutically acceptable salts. If the compounds I have at least one basic centre, they can form acid addition salts. These are formed, for example, with strong inorganic acids, such as mineral acids, for example sulfuric acid, a phosphoric acid or a hydrohalic acid, with strong organic carboxylic acids, such as unsubstituted or, for example, halo-substituted $C_1$-$C_4$alkanecarboxylic acids, for example acetic acid, saturated or unsaturated dicarboxylic acids, for example oxalic, malonic, succinic, maleic, fumaric, phthalic or terephthalic acid, hydroxycarboxylic acids, for example ascorbic, glycolic, lactic, malic, tartaric or citric acid, amino acids, for example aspartic or glutamic acid, or benzoic acid, or with organic sulfonic acids, such as unsubstituted or, for example, halo-substituted $C_1$-$C_4$alkane- or aryl-sulfonic acids, for example methane- or p-toluenesulfonic acid. Corresponding acid addition salts can also be formed with a basic centre that may be additionally present. Furthermore, compounds I having at least one acid group (for example COOH or 1H-tetrazol-5-yl) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropyl-amine, or a mono-, di- or tri-hydroxy-lower alkylamine, for example mono-, di- or tri-ethanolamine. Furthermore, corresponding internal salts may be formed. Also included are salts that are not suitable for pharmaceutical applications, which can be used, for example, for the isolation and purification of free compounds I or their pharmaceutically acceptable salts.

The rings A and B form a biphenylyl radical, corresponding biphenyl-4-yl being preferred and the radical $R_3$ preferably being located in a 2-position of ring B. Each of the rings A and B, independently of the other, is unsubstituted or mono- or poly-substituted, for example di- or tri-substituted, it being possible for the substituents to be selected from the group of the corresponding substituents listed above.

An aliphatic hydrocarbon radical is lower alkyl, lower alkenyl or, secondly, lower alkynyl.

An aliphatic hydrocarbon radical that is substituted by halogen or by hydroxy is halo-lower alkyl, -lower alkenyl or -lower alkynyl, or hydroxy-lower alkyl, -lower alkenyl or -lower alkynyl.

An aliphatic hydrocarbon radical that is substituted by halogen or by hydroxy in a position higher than the β-position with respect to the nitrogen atom shown in formula I is an aliphatic hydrocarbon radical substituted by halogen or by hydroxy and defined above, in which, however, the carbon atoms (C-atoms) in the α- and β-positions with respect to the nitrogen atom shown in formula I are unsubstituted.

An aliphatic hydrocarbon radical that is interrupted by O is lower alkoxy-lower alkyl, -lower alkenyl or -lower alkynyl, or lower alkenyloxy-lower alkyl, -lower alkenyl or -lower alkynyl.

An aliphatic hydrocarbon radical that is substituted by halogen or by hydroxy and interrupted by O is an aliphatic hydrocarbon radical that is interrupted by O and defined above and that is substituted by halogen or by hydroxy.

A cycloaliphatic hydrocarbon radical is cycloalkyl or, secondly, cycloalkenyl.

An araliphatic hydrocarbon radical is phenyl-lower alkyl or, secondly, phenyl-lower alkenyl or -lower alkynyl.

Straight-chained alkylene that is aliphatically bridged is straight-chained alkylene in which one or, independently of each other, two methylene group(s) has(have) been replaced by cycloalk-1,1-ylene.

Straight-chained alkylene that is substituted by an aliphatic hydrocarbon radical is straight-chained alkylene that is mono-, di-, tri- or tetra-substituted by a substituent or substituents selected from the group consisting of lower alkyl, lower alkenyl and, secondly, lower alkynyl.

Straight-chained alkylene that is bridged and substituted by an aliphatic hydrocarbon radical is straight-chained alkylene that is substituted by an aliphatic hydrocarbon radical and defined above and in which one or, independently of each other, two methylene group(s) of the methylene groups present in the corresponding unsubstituted straight-chained alkylene group has(have) been replaced by cycloalk-1,1-ylene.

Esterified carboxy is carboxy esterified by an alcohol the alcoholic hydroxy function of which is bonded to lower alkyl, lower alkenyl or lower alkynyl or to lower alkoxy-lower alkyl, -lower alkenyl or -lower alkynyl.

Amidated carboxy is carbamoyl in which the amino group is unsubstituted or is mono- or di-substituted by a substituent or substituents selected from the group consisting of lower alkyl, lower alkenyl, lower alkynyl and phenyl-lower alkyl, -lower alkenyl or -lower alkynyl, or is di-substituted by lower alkylene or by lower alkyleneoxy-lower alkylene.

Substituted amino is amino that is mono- or di-substituted by a substituent or substituents selected from the group consisting of lower alkyl, lower alkenyl, lower alkynyl and phenyl-lower alkyl, -lower alkenyl or -lower alkynyl, or is di-substituted by lower alkylene or by lower alkyleneoxy-lower alkylene.

Acylamino is amino mono-substituted by lower alkanoyl or by benzoyl.

Acetalised formyl is di-lower alkoxymethyl or 1,3-dioxacycloalk-2-yl.

Etherified hydroxy is lower alkoxy, lower alkenyloxy, phenoxy or benzyloxy.

Alkanoyl is lower alkanoyl.

N-substituted aminosulfonyl is aminosulfonyl in which the amino group is mono- or di-substituted by a substituent or substituents selected from the group consisting of lower alkyl, lower alkenyl, lower alkynyl and phenyl-lower alkyl, -lower alkenyl or -lower alkynyl, or is di-substituted by lower alkylene or by lower alkyleneoxy-lower alkylene.

S-substituted sulfonylamino is sulfonylamino in which the sulfur atom of the sulfonylamino group is mono-substituted by lower alkyl, lower alkenyl, lower alkynyl, halo-lower alkyl, -lower alkenyl or -lower alkynyl, phenyl-lower alkyl, -lower alkenyl or -lower alkynyl or by phenyl.

Hereinbefore and hereinafter, phenyl is in each case unsubstituted phenyl or phenyl that is mono- or poly-substituted, for example di- or tri-substituted, for example by a substituent or substituents selected from the group consisting of halogen, hydroxy, lower alkoxy, lower alkyl and trifluoromethyl. This applies to phenyl radicals per se and to phenyl part-structures in all groups comprising phenyl part-structures, that is to say in phenylene, phenyl-lower alkyl, phenyl-lower alkenyl, phenyl-lower alkynyl, benzoyl, phenoxy and benzyloxy groups.

Unless defined otherwise, the general terms used hereinbefore and hereinafter have the meanings given below.

The term "lower" means that groups and compounds so designated each comprise from 1 up to and including 7, preferably from 1 up to and including 4', carbon atoms.

Halogen is especially halogen having an atomic number of up to and including 35, that is to say fluorine, chlorine or bromine, and also includes iodine.

Straight-chained alkylene is straight-chained lower alkylene, that is to say straight-chained $C_1$–$C_7$alkylene, that is to say methylene, eth-1,2-ylene, prop-1,3-ylene, but-1,4-ylene, pent-1,5-ylene, hex-1,6-ylene or hept-1,7-ylene, the carbon atoms of these straight-chained alkylene groups being numbered in such a manner that the carbon atom adjacent to the group $(O)_p$ in formula I carries the number 1.

Haloalkanesulfonylamino is halo-lower alkanesulfonylamino, that is to say halo-$C_1$–$C_7$alkanesulfonylamino, and is, for example, trifluoromethane-, difluoromethane-, 1,1,2-trifluoroethane- or heptafluoropropane-sulfonylamino. Halo-$C_1$–$C_4$alkanesulfonylamino is preferred.

Phenylene is 1,2-, 1,3- or 1,4-phenylene.

Alkylene ($X_1$ and $X_2$) is especially $C_1$–$C_7$alkylene, is straight-chained or branched and is especially methylene, eth-1,2-ylene, prop-1,3-ylene, but-1,4-ylene, pent-1,5-ylene, prop-1,2-ylene, 2-methylprop-1,3-ylene or 2,2-dimethylprop-1,3-ylene. Straight-chained $C_1$–$C_3$alkylene is preferred.

Lower alkyl is $C_1$–$C_7$alkyl, that is to say methyl, ethyl, n-propyl, isopropyl, n-butyl, isobutyl, sec-butyl, tert-butyl or a corresponding pentyl, hexyl or heptyl radical. $C_1$–$C_4$alkyl is preferred.

Lower alkenyl is $C_3$–$C_7$alkenyl and is, for example, propen-2-yl, allyl or but-1-en-3-yl, -1-en-4-yl, -2-en-1-yl or -2-en-2-yl. $C_3$–$C_5$alkenyl is preferred.

Lower alkynyl is $C_3$–$C_7$alkynyl and is, for example, propargyl.

Halo-lower alkyl is especially halo-$C_1$–$C_4$alkyl, such as trifluoromethyl, 2-chloro-1,1,2-trifluoroethyl, chloromethyl, 3,3,3-trifluoropropyl, 4-chlorobutyl or heptafluoropropyl.

Halo-lower alkenyl is especially halo-$C_3$–$C_5$alkenyl, such as 3-chloroallyl.

Halo-lower alkynyl is especially halo-$C_3$–$C_5$alkynyl, such as 3-chloropropargyl.

Hydroxy-lower alkyl is especially hydroxy-$C_1$–$C_4$alkyl, such as hydroxymethyl, 2-hydroxyethyl, 3-hydroxypropyl or 4-hydroxybutyl.

Hydroxy-lower alkenyl is especially hydroxy-$C_3$–$C_5$alkenyl, such as 3-hydroxyallyl.

Hydroxy-lower alkynyl is especially hydroxy-$C_3$–$C_5$alkynyl, such as 3-hydroxypropargyl.

Lower alkoxy-lower alkyl is $C_1$–$C_4$alkoxy-$C_1$–$C_4$alkyl, such as 2-methoxyethyl, 2-ethoxyethyl, 2-(n-propoxy)ethyl or ethoxymethyl.

Lower alkoxy-lower alkenyl and lower alkoxy-lower alkynyl are $C_1$–$C_4$alkoxy-$C_3$–$C_5$alkenyl and $C_1$–$C_4$alkoxy-$C_3$–$C_5$alkynyl, respectively.

Lower alkenyloxy-lower alkyl is $C_3$–$C_5$alkenyloxy-$C_1$–$C_4$alkyl, such as 2-allyloxyethyl, and lower alkenyloxy-lower alkenyl and lower alkenyloxy-lower alkynyl are $C_3$–$C_5$alkenyloxy-$C_3$–$C_5$alkenyl and $C_3$–$C_5$alkenyloxy-$C_3$–$C_5$alkynyl, respectively.

Cycloalkyl is cyclo-lower alkyl, that is to say $C_3$–$C_7$cycloalkyl, that is to say cyclopropyl, cyclobutyl, cyclopentyl, cyclohexyl or cycloheptyl. Cyclopentyl and cyclohexyl are preferred.

Cycloalkenyl is cyclo-lower alkenyl, that is to say $C_3$–$C_7$cycloalkenyl, and is, for example, cyclopent-2-enyl or -3-enyl or cyclohex-2-enyl or -3-enyl.

Phenyl-lower alkyl is phenyl-$C_1$–$C_4$alkyl and is, for example, benzyl or 1- or 2-phenethyl, whilst phenyl-lower alkenyl and phenyl-lower alkynyl are phenyl-$C_3$–$C_5$alkenyl and phenyl-$C_3$–$C_5$alkynyl, respectively, for example 3-phenylallyl or 3-phenylpropargyl. Cycloalk-1,1-ylene is cyclo-lower alk-1,1-ylene, that is to say $C_3$–$C_7$cycloalk-1,1-ylene, that is to say cycloprop-1,1-ylene, cyclobut-1,1-ylene, cyclopent-1,1-ylene, cyclohex-1,1-ylene or cyclohept-1,1-ylene.

Lower alkylene (which, in accordance with the definition, does not need to be identical with the straight-chained alkylene X defined above) is $C_2$–$C_7$alkylene, is straight-chained or branched and is especially eth-1,2- ylene, prop-1,3-ylene, but-1,4-ylene, pent-1,5-ylene, prop-1,2-ylene, 2-methylprop-1,3-ylene or 2,2-dimethylprop-1,3-ylene. $C_2$-$C_5$alkylene is preferred.

Lower alkyleneoxy-lower alkylene is $C_2$-$C_4$alkyleneoxy-$C_2$-$C_4$alkylene, for example ethyleneoxyethylene.

Lower alkanoyl is $C_1$-$C_7$alkanoyl and is, for example, formyl, acetyl, propionyl, butyryl, isobutyryl or pivaloyl. $C_2$-$C_5$alkanoyl is preferred.

Halo-lower alkanesulfonyl is halo-$C_1$-$C_7$alkanesulfonyl, such as trifluoromethanesulfonyl.

Di-lower alkoxymethyl is especially di-$C_1$-$C_4$alkoxymethyl, for example dimethoxymethyl or diethoxymethyl.

1,3-Dioxacycloalk-2-yl is 1,3-dioxa-$C_4$-$C_7$cycloalk-2-yl, for example 1,3-dioxacyclopent-2-yl or 1,3-dioxacyclohex-2-yl.

Lower alkoxy is $C_1$-$C_7$alkoxy, that is to say methoxy, ethoxy, n-propoxy, isopropoxy, n-butoxy, isobutoxy, sec-butoxy, tert-butoxy or corresponding pentyloxy, hexyloxy or heptyloxy. $C_1$-$C_4$alkoxy is preferred.

Lower alkenyloxy is $C_3$-$C_7$alkenyloxy and is, for example, allyloxy, but-2-en-1-yloxy or but-3-en-1-yloxy. $C_3$-$C_5$alkenyloxy is preferred.

Extensive pharmacological research has shown that the compounds I and their pharmaceutically acceptable salts have, for example, pronounced angiotensin II antagonistic properties.

Angiotensin II is known to have pronounced vasoconstrictive properties and, moreover, to stimulate aldosterone secretion, thus causing marked sodium/water retention. The result of angiotensin II activity manifests itself inter alia in an increase in blood pressure.

The importance of angiotensin II antagonists lies in the suppression, by competitive inhibition of the binding of angiotensin II to the receptors, of the effects of vasoconstriction and of stimulation of aldosterone secretion produced by angiotensin II.

The angiotensin II antagonistic properties of the compounds I and their pharmaceutically acceptable salts can be detected in an angiotensin II binding test. In that test, smooth muscle cells from homogenised rat aorta are used. The solid centrifugate is suspended in 50 mM Tris buffer (pH 7.4) with the use of peptidase inhibitors. The samples are incubated at 25° C. for 60 minutes with $^{125}$I-angiotensin II (0.175 nM) and a varying concentration of angiotensin II or of test compound. The incubation is then stopped by the addition of ice-cold-phosphate-buffered saline and the batch is filtered through Whatman GF/F filters. The filters are counted using a gamma-counter. The $IC_{50}$ values are determined from the dose/activity curve. $IC_{50}$ values of approximately 10 nM and above are found for the compounds I and their pharmaceutically acceptable salts.

Tests on isolated rings of rabbit aorta can be used to determine angiotensin II induced vasoconstriction. For that purpose, rings of aorta are dissected from each thorax and are fixed between two parallel clips at an initial tension of 2 g. The rings are then immersed in 20 ml of a tissue bath at 37° C. and gassed with a mixture of 95% $O_2$ and 5% $CO_2$. The isometric reactions are measured. At 20-minute intervals, the rings are stimulated alternately with 10 nM angiotensin II (Hypertensin-CIBA) and 5 nM noradrenalin chloride. The rings are then incubated with selected concentrations of the test compounds before being treated with the agonists. The data are analysed with a Buxco digital computer. The concentrations that bring about a 50% inhibition of the initial control values are given as the $IC_{50}$ values. $IC_{50}$ values of approximately 5 nM and above are found for the compounds I and their pharmaceutically acceptable salts.

The fact that the compounds I and their pharmaceutically acceptable salts are able to reduce high blood pressure induced by angiotensin II can be verified using the test model of the normotensive anaesthetised rat. After calibration of the preparations using 0.9% NaCl (1 ml/kg i.v.) and noradrenalin (1 μg/kg i.v.) or angiotensin II (0.3 μg/kg i.v.), respectively, increasing doses (3-6) of the test compound are injected intravenously by means of bolus injection, whereupon after each dose angiotensin II or noradrenalin is administered at 5-minute intervals. The blood pressure is measured directly at the carotid and recorded using an on-line data-recording system (Buxco). The specificity of the angiotensin II antagonism is indicated by the selective inhibition of the pressure effect caused by angiotensin II but not of that caused by noradrenalin. In this test model, the compounds I and their pharmaceutically acceptable salts exhibit an inhibiting effect at a dose of approximately from 0.3 mg/kg i.v. and above.

The antihypertensive activity of the compounds I and their pharmaceutically acceptable salts can also be demonstrated using the test model of the renally hypertensive rat. High blood pressure is induced in male rats by constriction of a renal artery in accordance with the Goldblatt method. Doses of the test compound are administered to the rats by means of a stomach probe. Control animals receive an equivalent volume of solvent. Blood pressure and heart beat are measured indirectly, at intervals, in conscious animals using the tail-clamping method of Gerold et al. [*Helv. Physiol. Acta* 24 (1966), 58] both before administration of the test compound or the solvent and during the course of the experiments. The pronounced antihypertensive effect can be detected at a dose of approximately 30 mg/kg p.o. and above.

The compounds I and their pharmaceutically acceptable salts can accordingly be used, for example, as active ingredients in antihypertensive drugs which are used, for example, for the treatment of high blood pressure and cardiac insufficiency. The invention therefore relates to the use of the compounds I and their pharmaceutically acceptable salts for the preparation of corresponding medicaments and for the therapeutic treatment of high blood pressure and of cardiac insufficiency. The preparation of the medicaments also includes the commercial manufacture of the active ingredients.

Preferred are compounds of formula I wherein $R_1$ is lower alkyl, lower alkenyl, lower alkynyl, halo-lower alkyl, -lower alkenyl or -lower alkynyl carrying halogen in a position higher than the β-position with respect to the nitrogen atom shown in formula I, hydroxy-lower alkyl, -lower alkenyl or -lower alkynyl carrying hydroxy in a position higher than the β-position with respect to the nitrogen atom shown in formula I, cyclo-lower alkyl, cyclo-lower alkenyl, phenyl-lower alkyl or phenyl-lower alkenyl or -lower alkynyl; $R_2$ is 1H-tetrazol-5-yl, carboxy, carboxy esterified by an alcohol the alcoholic hydroxy function of which is bonded to lower alkyl, lower alkenyl or lower alkynyl or to lower alkoxy-lower alkyl, -lower alkenyl or -lower alkynyl, or is carbamoyl in which the amino group is unsubstituted or is mono- or di-substituted by a substituent or substituents selected from the group consisting of lower alkyl, lower alkenyl, lower alkynyl and phenyl-lower alkyl, -lower alkenyl and -lower alkynyl, or is di-substituted by lower alkylene or by lower alkyleneoxy-lower alkylene, or is amino, amino that is mono- or di-substituted by a substituent or substituents selected from the group consisting of lower alkyl, lower alkenyl, lower alkynyl and phenyl-lower alkyl, -lower alkenyl and -lower alkynyl, or is di-substituted by lower alkylene or by lower alkyleneoxy-lower alkylene, or amino that is mono-substituted by lower alkanoyl or by benzoyl, or is formyl, di-lower alkoxymethyl, 1,3-dioxacycloalk-2-yl, hydroxy, lower alkoxy, lower alkenyloxy, phenoxy, benzyloxy, $S(O)_m$-R, wherein m is 0, 1 or 2 and R is hydrogen, lower alkyl, lower alkenyl or lower alkynyl, or lower alkanoyl, aminosulfonyl, aminosulfonyl in which the amino group is mono- or di-substituted by a substituent or substituents selected from the group consisting of lower alkyl, lower alkenyl, lower alkynyl and phenyl-lower alkyl, -lower alkenyl and -lower alkynyl, or is di-substituted by lower alkylene or by lower alkyleneoxy-lower alkylene, or $PO_2H_2$, $PO_3H_2$ or sulfonylamino in which the sulfur atom of the sulfonylamino group is mono-substituted by lower alkyl, lower alkenyl, lower alkynyl, halo-lower alkyl, -lower alkenyl or -lower alkynyl, phenyl-lower alkyl, -lower alkenyl or -lower alkynyl or by phenyl; $R_3$ is carboxy, 1H-tetrazol-5-yl, $SO_3H$, $PO_2H_2$, $PO_3H_2$ or halo-lower alkanesulfonylamino; X is straight-chained lower alkylene, straight-chained lower alkylene in which one or, independently of each other, two methylene group(s) has(have) been replaced by cyclo-lower alk-1,1-ylene, straight-chained lower alkylene that is mono-, di-, tri- or tetra-substituted by a substituent or substituents selected from the group consisting of lower alkyl, lower alkenyl and lower alkynyl, or straight-chained lower alkylene that is mono-, di-, tri- or tetra-substituted by a substituent or substituents selected from the group consisting of lower alkyl, lower alkenyl and lower alkynyl and in which one or, independently of each other, two methylene group(s) of the methylene groups present in the corresponding unsubstituted straight-chained lower alkylene group has(have) been replaced by cyclo-lower alk-1,1-ylene, or is the structural element of the formula —$X_1$—Ph—$X_2$—, wherein each of $X_1$ and $X_2$, independently of the other, is a bond or $C_1$–$C_7$alkylene and Ph is phenylene; wherein each of the rings A and B, independently of the other, is unsubstituted or is substituted by halogen, hydroxy, lower alkoxy, lower alkenyloxy, phenoxy, benzyloxy, $S(O)_m$—R, wherein m is 0, 1 or 2 and R is hydrogen, lower alkyl, lower alkenyl or lower alkynyl, or by lower alkyl, lower alkenyl, lower alkynyl, halo-lower alkyl, -lower alkenyl or -lower alkynyl, hydroxy-lower alkyl, -lower alkenyl or -lower alkynyl, or by unsubstituted or halo- or hydroxy-substituted lower alkoxy-lower alkyl, -lower alkenyl or -lower alkynyl, or unsubstituted or halo- or hydroxy-substituted lower alkenyloxy-lower alkyl, -lower alkenyl or -lower alkynyl; and either p and q are both 1 or p is 0 and q is 0 or 1; wherein phenyl in phenyl radicals per se and in phenylene, phenyl-lower alkyl, phenyl-lower alkenyl, phenyl-lower alkynyl, benzoyl, phenoxy and benzyloxy groups is in each case unsubstituted phenyl or phenyl mono- or poly-substituted by a substituent or substituents selected from the group consisting of halogen, hydroxy, lower alkoxy, lower alkyl and trifluoromethyl; in free form or in salt form.

Especially preferred are compounds of formula I wherein $R_1$ is lower alkyl, lower alkenyl or cyclo-lower alkyl; $R_2$ is 1H-tetrazol-5-yl, carboxy, carboxy esterified by an alcohol the alcoholic hydroxy function of which is bonded to lower alkyl, lower alkenyl or lower alkynyl or to lower alkoxy-lower alkyl, -lower alkenyl or -lower alkynyl, or is carbamoyl in which the amino group is unsubstituted or is mono- or di-substituted by a substituent or substituents selected from the group consisting of lower alkyl, lower alkenyl, lower alkynyl and phenyl-lower alkyl, -lower alkenyl and -lower alkynyl, or is di-substituted by lower alkylene or by lower alkyleneoxy-lower alkylene, or is amino, amino that is mono- or di-substituted by a substituent or substituents selected from the group consisting of lower alkyl, lower alkenyl, lower alkynyl and phenyl-lower alkyl, -lower alkenyl and -lower alkynyl, or is di-substituted by lower alkylene or by lower alkyleneoxy-lower alkylene, or amino that is mono-substituted by lower alkanoyl or by benzoyl, or is formyl, di-lower alkoxymethyl, 1,3-dioxacycloalk-2-yl, hydroxy, lower alkoxy, lower alkenyloxy, phenoxy, benzyloxy, $S(O)_m$—R, wherein m is 0, 1 or 2 and R is hydrogen, lower alkyl, lower alkenyl or lower alkynyl, or lower alkanoyl, aminosulfonyl, aminosulfonyl in which the amino group is mono- or di-substituted by a substituent or substituents selected from the group consisting of lower alkyl, lower alkenyl, lower alkynyl and phenyl-lower alkyl, -lower alkenyl and -lower alkynyl, or is di-substituted by lower alkylene or by lower alkyleneoxy-lower alkylene, or $PO_2H_2$, $PO_3H_2$ or sulfonylamino in which the sulfur atom of the sulfonylamino group is mono-substituted by lower alkyl, lower alkenyl, lower alkynyl, halo-lower alkyl, -lower alkenyl or -lower alkynyl, phenyl-lower alkyl, -lower alkenyl or -lower alkynyl or by phenyl; $R_3$ is carboxy, 1H-tetrazol-5-yl or halo-lower alkanesulfonylamino; X is straight-chained lower alkylene, straight-chained lower alkylene in which one methylene group has been replaced by cyclo-lower alk-1,1-ylene, straight-chained lower alkylene that is mono-, di-, tri- or tetra-substituted by a substituent or substituents selected from the group consisting of lower alkyl, lower alkenyl and lower alkynyl, or straight-chained lower alkylene that is mono- or di-substituted by a substituent or substituents selected from the group consisting of lower alkyl, lower alkenyl and lower alkynyl and in which one methylene group of the methylene groups present in the corresponding unsubstituted straight-chained lower alkylene group has been replaced by cyclo-lower alk-1,1-ylene; or X is the structural element of the formula —$X_1$—Ph—$X_2$—, wherein each of $X_1$ and $X_2$, independently of the other, is a bond or $C_1$–$C_7$alkylene and Ph is phenylene; each of the rings A and B, independently of the other, is unsubstituted or is substituted by halogen, hydroxy, lower alkoxy, $S(O)$-$m$—R, wherein m is 0, 1 or 2 and R is hydrogen or lower alkyl, or by lower alkyl, halo-lower alkyl, hydroxy-lower alkyl, unsubstituted or halo- or hydroxy-substituted lower alkoxy-lower alkyl or by unsubstituted or halo- or hydroxy-substituted lower alkenyloxy-lower alkyl; and either p and q are both 1 or p is 0 and q is 0 or 1; wherein phenyl in phenyl radicals per se and in phenylene, phenyl-lower alkyl, phenyl-lower alkenyl, phenyl-lower alkynyl, benzoyl, phenoxy and benzyloxy groups is in each case unsubstituted phenyl or phenyl mono- or di-substituted by a substituent or substituents selected from the group consisting of halogen, hydroxy, lower alkoxy, lower alkyl and trifluoromethyl; in free form or in salt form.

Most especially preferred are compounds of formula I wherein $R_1$ is lower alkyl or lower alkenyl; $R_2$ is 1H-tetrazol-5-yl, carboxy, carboxy esterified by an alcohol the alcoholic hydroxy function of which is bonded to lower alkyl or to lower alkoxy-lower alkyl, or is carbamoyl in which the amino group is unsubstituted or is mono- or di-substituted by a substituent or substituents selected from the group consisting of lower alkyl and phenyl-lower alkyl, or is di-substituted by lower alkylene or by lower alkyleneoxy-lower alkylene, or is amino, amino that is mono- or di-substituted by a substituent or substituents selected from the group consisting of lower alkyl and phenyl-lower alkyl, or is di-substituted by lower alkylene or by lower alkyleneoxy-lower alkylene, or amino that is mono-substituted by lower alkanoyl, or is hydroxy, lower alkoxy, phenoxy, benzyloxy, $S(O)_m$—R, wherein m is 0, 1 or 2 and R is hydrogen or lower alkyl, or lower alkanoyl, aminosulfonyl, $PO_2H_2$, $PO_3H_2$ or sulfonylamino in which the sulfur atom of the sulfonylamino group is mono-substituted by lower alkyl, halo-lower alkyl, phenyl-lower alkyl or by phenyl; $R_3$ is carboxy or 1H-tetrazol-5-yl; X is straight-chained lower alkylene, straight-chained lower alkylene in which one methylene group has been replaced by cyclo-lower alk-1,1-ylene, or straight-chained lower alkylene that is mono-substituted by a lower alkyl substituent or di-substituted by identical or different lower alkyl substituents, or X is the structural element of the formula —$X_1$—Ph—$X_2$—, wherein each of $X_1$ and $X_2$, independently of the other, is a bond or $C_1$–$C_7$alkylene and Ph is phenylene; each of the rings A and B, independently of the other, is unsubstituted or is substituted by halogen, hydroxy, lower alkoxy, $S(O)_m$—R, wherein m is 0, 1 or 2 and R is hydrogen or lower alkyl, or by lower alkyl; p is 0, q is 0 or 1; and the ring B is bonded in the 4-position of the ring A; wherein phenyl in phenylene, phenyl-lower alkyl, phenoxy and benzyloxy groups is in each case unsubstituted phenyl or phenyl mono-substituted by a substituent selected from the group consisting of halogen, lower alkoxy, lower alkyl and trifluoromethyl; in free form or in salt form.

Especially preferred are compounds of formula I wherein the rings A and B are unsubstituted; p is 0; q is 1; the ring B is bonded in the 4-position of the ring A; and $R_3$ is bonded in a 2-position of the ring B; in free form or in salt form.

Especially preferred are compounds of formula I wherein $R_1$ is $C_1$–$C_4$alkyl, such as propyl or butyl, or $C_3$–$C_5$alkenyl, such as allyl; $R_2$ is 1H-tetrazol-5-yl, carboxy, $C_1$–$C_4$alkoxycarbonyl, such as methoxy- or ethoxy-carbonyl, carbamoyl, N-$C_1$–$C_4$alkylcarbamoyl, such as N-methylcarbamoyl, N,N-di-$C_1$–$C_4$alkylcarbamoyl, such as N,N-dimethylcarbamoyl, $C_1$–$C_4$alkanoyl, such as acetyl, aminosulfonyl or sulfonylamino in which the sulfur atom of the sulfonylamino group is mono-substituted by $C_1$–$C_4$alkyl, such as methyl; $R_3$ is carboxy or 1H-tetrazol-5-yl; X is straight-chained $C_1$–$C_7$alkylene, such as eth-1,2-ylene, prop-1,3-ylene, but-1,4-ylene or pent-1,5-ylene, in which one methylene group has been replaced by $C_3$–$C_7$cycloalk-1,1-ylene, such as cyclopent-1,1-ylene or cyclohex-1,1-ylene, or is straight-chained $C_1$–$C_7$alkylene, such as methylene, eth-1,2-ylene, prop-1,3-ylene or but-1,4-ylene, that is mono-substituted by a $C_1$–$C_4$alkyl, such as methyl or ethyl, substituent or di-substituted by identical or different $C_1$–$C_4$alkyl, such as methyl or ethyl, substituents; the rings A and B are unsubstituted; p is 0; q is 1; the ring B is bonded in the 4-position of the ring A; and $R_3$ is bonded in a 2-position of the ring B; in free form or in salt form.

Especially preferred are compounds of formula I wherein $R_1$ is $C_1$–$C_4$alkyl, such as propyl or butyl, or $C_3$–$C_5$alkenyl, such as allyl; $R_2$ is 1H-tetrazol-5-yl, carboxy, $C_1$–$C_4$alkoxycarbonyl, such as methoxy- or ethoxy-carbonyl, carbamoyl, N-$C_1$–$C_4$alkylcarbamoyl, such as N-methylcarbamoyl, N,N-di-$C_1$–$C_4$alkylcarbamoyl, such as N,N-dimethylcarbamoyl, $C_1$–$C_4$alkanoyl, such as acetyl, aminosulfonyl or sulfonylamino in which the sulfur atom of the sulfonylamino group is mono-substituted by $C_1$–$C_4$alkyl, such as methyl; $R_3$ is carboxy or 1H-tetrazol-5-yl; X is the structural element of the formula —$X_1$—Ph—$X_2$—, wherein each of $X_1$ and $X_2$, independently of the other, is a bond or straight-chained $C_1$–$C_3$alkylene, especially methylene, and Ph is phenylene, such as 1,2- or 1,3-phenylene; the rings A and B are unsubstituted; p is 0, q is 1; the ring B is bonded in the 4-position of the ring A; and $R_3$ is bonded in a 2-position of the ring B; in free form or in salt form.

More especially preferred are compounds of formula I wherein $R_1$ is $C_1$–$C_4$alkyl, such as propyl or butyl; $R_2$ is carboxy, $C_1$–$C_4$alkoxycarbonyl, such as methoxycarbonyl, or carbamoyl; $R_3$ is 1H-tetrazol-5-yl; X is straight-chained $C_1$–$C_7$alkylene, such as eth-1,2-ylene, prop-1,3-ylene, but-1,4-ylene or pent-1,5-ylene, in which one methylene group has been replaced by $C_3$–$C_7$cycloalk-1,1-ylene, such as cyclopent-1,1-ylene, or is straight-chained $C_1$–$C_7$alkylene, such as methylene, eth-1,2-ylene, prop-1,3-ylene or but-1,4-ylene, that is mono-substituted by a $C_1$–$C_4$alkyl, such as methyl or ethyl, substituent or di-substituted by identical or different $C_1$–$C_4$alkyl, such as methyl or ethyl, substituents; the rings A and B are unsubstituted; p is 0; q is 1; the ring B is bonded in the 4-position of the ring A; and $R_3$ is bonded in a 2-position of the ring B; in free form or in salt form.

Most especially preferred are compounds of formula I wherein $R_1$ is $C_1$–$C_4$alkyl, such as propyl or butyl; $R_2$ is carboxy; $R_3$ is 1H-tetrazol-5-yl; X is straight-chained $C_1$–$C_7$alkylene, such as eth-1,2-ylene, prop-1,3-ylene, but-1,4-ylene or pent-1,5-ylene, in which one methylene group has been replaced by $C_3$–$C_7$cycloalk-1,1-ylene, such as cyclopent-1,1-ylene, or is straight-chained $C_1$–$C_7$alkylene, such as methylene, eth-1,2-ylene, prop-1,3-ylene or but-1,4-ylene, that is mono-substituted by a $C_1$–$C_4$alkyl, such as methyl or ethyl, substituent or di-substituted by identical or different $C_1$–$C_4$alkyl, such as methyl or ethyl, substituents; the rings A and B are unsubstituted; p is 0; q is 1; the ring B is bonded in the 4-position of the ring A; and $R_3$ is bonded in a 2-position of the ring B; in free form or in salt form.

Most especially preferred are compounds of formula I wherein $R_1$ is $C_3$–$C_4$alkyl, such as n-propyl or n-butyl; $R_2$ is carboxy; $R_3$ is 1H-tetrazol-5-yl; X is 2-methylbut-1,3-ylene or is 1,3-propylene in which the $\omega$-methylene group has been replaced by cyclohex-1,1-ylene; the rings A and B are unsubstituted; p is 0; q is 1; the ring B is bonded in the 4-position of the ring A; and $R_3$ is bonded in a 2-position of the ring B; in free form or in salt form.

Specifically preferred are the compounds of formula I mentioned in the Examples, in free form or in salt form.

The invention further relates to a process for the preparation of the compounds I and their salts, for example wherein a) in a compound of formula

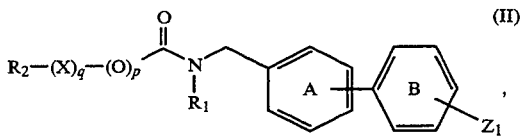

wherein $Z_1$ is a radical that can be converted into $R_3$, or in a salt thereof, $Z_1$ is converted into $R_3$ or b) a compound of formula

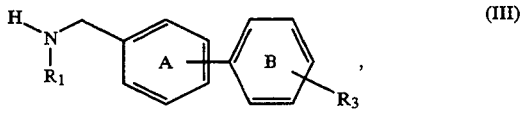

or a salt thereof, is reacted with a compound of formula

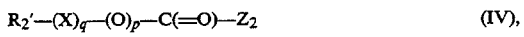

wherein either $C(=O)—Z_2$ is a carboxy group or a reactive derivative thereof and $R_2'$ is a radical $R_2$ or wherein $R_2'$ and $C(=O)—Z_2$ together form the group $—C(=O)—O—C(=O)—$, or with a salt thereof, and in each case, if desired, a compound I obtainable in accordance with the process or by another method, in free form or in salt form, is converted into a different compound I, a mixture of isomers obtainable in accordance with the process is separated and the desired isomer is isolated and/or a free compound I obtainable in accordance with the process is converted into a salt or a salt of a compound I obtainable in accordance with the process is converted into the free compound I or into a different salt.

Salts of starting materials that have at least one basic centre are corresponding acid addition salts, whilst salts of starting materials that have at least one acid group are salts with bases, in each case as mentioned above in connection with corresponding salts of compounds I.

The reactions described hereinbefore and hereinafter in the variants are carried out in a manner known per se, for example in the absence or, customarily, in the presence of a suitable solvent or diluent or of a mixture thereof and, as required, with cooling, at room temperature or with heating, for example within a temperature range of from approximately $-80°$ C. to the boiling temperature of the reaction medium, preferably from approximately $-10°$ to approximately $+200°$ C., and, if necessary, in a closed vessel, under pressure, in an inert gas atmosphere and/or under anhydrous conditions. Details of corresponding procedures and reaction conditions can be gathered especially from the Examples.

Variant a)

Radicals $Z_1$ that can be converted into the variables $R_3$ are, for example, cyano, mercapto, halogen, the group $—N_2^+A^-$, in which $A^-$ is an anion derived from an acid, amino, functional derivatives of COOH, $SO_3H$, $PO_3H_2$ and $PO_2H_2$ and protected 1H-tetrazol-5-yl.

Radicals $Z_1$ that can be converted into 1H-tetrazol-5-yl $R_3$ are, for example, cyano and protected 1H-tetrazol-5-yl.

For the preparation of compounds I wherein $R_3$ is 1H-tetrazol-5-yl, there is used, for example, a starting material II wherein $Z_1$ is cyano, which is reacted, for example in an inert solvent, for example in an aromatic or araliphatic hydrocarbon, for example in toluene or a xylene, preferably with heating, with an azide, for example with $HN_3$ or, especially, a salt, such as an alkali metal salt, thereof, or with an organotin azide, such as a tri-lower alkyl- or triaryl-tin azide. Preferred azides are, for example, sodium and potassium azide and also tri-$C_1$-$C_4$alkyltin azide, for example trimethyl- or tributyl-tin azide, and triphenyltin azide.

Suitable protecting groups of protected 1H-tetrazol-5-yl are the protecting groups customarily used in tetrazole chemistry, especially triphenylmethyl, unsubstituted or, for example, nitro-substituted benzyl, such as 4-nitrobenzyl, lower alkoxymethyl, such as methoxy- or ethoxy-methyl, lower alkylthiomethyl, such as methylthiomethyl, and 2-cyanoethyl, and also lower alkoxylower alkoxymethyl, such as 2-methoxyethoxymethyl, benzyloxymethyl and phenacyl. The removal of the protecting groups is carried out in accordance with known methods. For example, triphenylmethyl is customarily removed by hydrolysis, especially in the presence of an acid, for example in the presence of a hydrogen halide, advantageously in an inert solvent, such as a haloalkane or an ether, for example in dichloromethane or dioxane, and with heating, or by hydrogenolysis in the presence of a hydrogenation catalyst, 4-nitrobenzyl being removed, for example, by hydrogenolysis in the presence of a hydrogenation catalyst, methoxy- or ethoxy-methyl being removed, for example, by treatment with a tri-lower alkyltin bromide, such as triethyl- or tributyl-tin bromide, methylthiomethyl being removed, for example, by treatment with trifluoroacetic acid, 2-cyanoethyl being removed, for example, by hydrolysis, for example with sodium hydroxide solution, 2-methoxyethoxymethyl being removed, for example, by hydrolysis, for example with hydrochloric acid, and benzyloxymethyl and phenacyl being removed, for example, by hydrogenolysis in the presence of a hydrogenation catalyst.

A radical $Z_1$ that can be converted into $SO_3H$ $R_3$ is, for example, a mercapto group. Starting materials II having such a group are oxidised, for example by oxidation methods known per se, to compounds I wherein $R_3$ is $SO_3H$. Suitable oxidising agents are, for example, inorganic peracids, such as peracids of mineral acids, for example periodic acid or persulfuric acid, organic peracids, such as percarboxylic and persulfonic acids, for example performic, peracetic, trifluoroperacetic or perbenzoic acid or p-toluenepersulfonic acid, or mixtures of hydrogen peroxide and acids, for example mixtures of hydrogen peroxide and acetic acid. The oxidation is frequently carried out in the presence of suitable catalysts, there being mentioned as catalysts suitable acids, such as unsubstituted or substituted carboxylic acids, for example acetic acid or trifluoroacetic acid, or transition metal oxides, such as oxides of elements of sub-group VI, for example molybdenum oxide or tungsten oxide. The oxidation is carried out under mild conditions, for example at temperatures of from approximately $-50°$ to approximately $+100°$ C.

There is to be understood by a group that can be converted into $PO_3H_2R_3$, for example, a group $—N_2$-$^+A^{31}$, wherein $A^-$ is the anion of an acid, such as a mineral acid. Corresponding diazonium compounds are reacted, for example, in a manner known per se with a P(III) halide, such as $PCl_3$ or $PBr_3$, and worked up by hydrolysis, it being possible to obtain compounds I wherein $R_3$ is $PO_3H_2$.

Compounds I wherein $R_3$ is $PO_2H_2$ are obtained, for example, by conversion, in the customary manner, of $Z_1$ in a compound II wherein $Z_1$ is a functional derivative of $PO_2H_2$ into $PO_2H_2$.

A suitable radical $Z_1$ that can be convened into haloalkanesulfonylamino $R_3$ is, for example, amino. For the preparation of compounds I wherein $R_3$ is haloalkanesulfonylamino, corresponding anilines, for example, are reacted with a customarily reactively esterified haloalkanesulfonic acid, the reaction being carried out where appropriate in the presence of a base. Preferred reactively esterified haloalkanesulfonic acids are the corresponding halides, such as chlorides, for example trifluoromethanesulfonyl chloride, and the corresponding anhydrides, for example trifluoromethanesulfonic acid anhydride.

A radical $Z_1$ that can be convened into COOH $R_3$ is, for example, functionally modified carboxy, such as cyano, esterified or amidated carboxy, hydroxymethyl or formyl.

Esterified carboxy is, for example, carboxy esterified by an unsubstituted or substituted aliphatic, cycloaliphatic or aromatic alcohol. An aliphatic alcohol is, for example, a lower alkanol, such as methanol, ethanol, n-propanol, isopropanol, n-butanol, sec-butanol or tert-butanol, whilst a suitable cycloaliphatic alcohol is, for example, a 3- to 8-membered cycloalkanol, such as cyclopentanol, cyclohexanol or cycloheptanol. An aromatic alcohol is, for example, a phenol or a heterocyclic alcohol, each of which may be substituted, especially hydroxypyridine, for example 2-, 3- or 4-hydroxypyridine.

Amidated carboxy is, for example, carbamoyl, carbamoyl mono-substituted by hydroxy, amino or by unsubstituted or substituted phenyl, carbamoyl mono- or di-substituted by lower alkyl, or carbamoyl di-substituted by 4- to 7-membered alkylene or by 3-aza-, 3-lower alkylaza-, 3-oxa- or 3-thia-alkylene. Examples are carbamoyl, N-mono- or N,N-di-lower alkylcarbamoyl, such as N-methyl-, N-ethyl, N,N-dimethyl-, N,N-diethyl-and N,N-dipropyl-carbamoyl, pyrrolidino- and piperidino-carbonyl, morpholino-, piperazino-, 4-methylpiperazino- and thiomorpholino-carbonyl, anilinocarbonyl and anilinocarbonyl substituted by lower alkyl, lower alkoxy and/or by halogen.

Preferred functionally modified carboxy is lower alkoxycarbonyl, such as methoxycarbonyl or ethoxycarbonyl, and cyano.

Compounds I wherein $R_3$ is carboxy can be prepared, for example, using compounds II wherein $Z_1$ is cyano or esterified or amidated carboxy as starting materials, by hydrolysis, especially in the presence of a base, or, using compounds II wherein $Z_1$ is hydroxymethyl or formyl as starting materials, by oxidation. The oxidation is effected, for example, in an inert solvent, such as a lower alkanecarboxylic acid, for example acetic acid, a ketone, for example acetone, an ether, for example tetrahydrofuran, a heterocyclic aromatic compound, for example pyridine, or in water, or in a mixture thereof, if necessary with cooling or heating, for example in a temperature range of from approximately 0° to approximately +150° C. Suitable oxidising agents are, for example, oxidising transition metal compounds, especially those with elements of sub-group I, VI or VII. Examples which may be mentioned are silver compounds, such as silver nitrate, silver oxide and silver picolinate, chromium compounds, such as chromium trioxide and potassium dichromate, and manganese compounds, such as potassium permanganate, tetrabutylammonium permanganate and benzyltriethylammonium permanganate. Other oxidising agents are, for example, suitable compounds with elements of main group IV, such as lead dioxide, or halogen-oxygen compounds, such as sodium iodate or potassium periodate.

The starting material II is obtainable in a manner analogous to known methods, for example by reacting a compound of formula

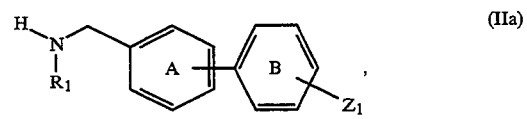

(IIa)

or a salt thereof, with a compound $R_2'$—$(X)_q$—(O)-$_p$—C($=$O)—$Z_2$ (IV), or a salt thereof, for example in a manner analogous to that described under process variant b) for the reaction of compounds III and IV.

Compounds II obtainable in this manner and wherein $R_2$ is carboxy may, if desired, be converted into compounds II wherein $R_2$ is esterified carboxy, for example lower alkoxycarbonyl, in a manner known per se before being reacted to form compounds I.

The compounds IV are known or can be prepared in a manner known per se.

The compounds IIa are obtainable in a manner analogous to known methods, for example by reacting a compound of formula $R_1$—$NH_2$ (IIb), or a salt thereof, in customary manner with a compound of formula

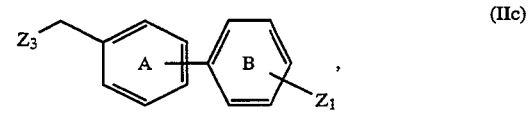

(IIc)

wherein $Z_3$ is a nucleofugal leaving group, such as halogen, for example chlorine or bromine, hydroxy, lower alkoxy, for example methoxy or ethoxy, lower alkylthio, for example methylthio, unsubstituted or substituted amino, for example amino, N-lower alkylamino or N,N-di-lower alkylamino, or sulfonyloxy, for example optionally halogenated lower alkanesulfonyloxy or unsubstituted or substituted benzenesulfonyloxy, such as methane-, ethane-, trifluoromethane-, benzene- or p-toluene-sulfonyloxy, or with a salt thereof.

The compounds IIb and IIc are known or can be prepared in a manner known per se (cf. EP 253,310).

Variant b)

Reactive derivatives of a carboxy group C($=$O)—$Z_2$ are, for example, activated esters, reactive anhydrides and reactive cyclic amides each derived from carboxy.

Activated esters derived from carboxy are, for example, esters that are unsaturated at the linking carbon atom of the esterifying radical, for example esters of the vinyl ester type, such as vinyl esters (obtainable, for example, by transesterification of a corresponding ester with vinyl acetate; activated vinyl ester method), carbamoylvinyl esters (obtainable, for example, by treatment of the corresponding acid with an isoxazolium reagent; 1,2-oxazolium or Woodward method) or 1-lower alkoxyvinyl esters (obtainable, for example, by treatment of the corresponding acid with a lower alkoxyacetylene; ethoxyacetylene method), esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method) or N,N-disubstituted amidino esters (obtainable, for example, by treatment of the corresponding acid with an N,N-disubstituted cyanamide; cyanamide method) or suitable aryl esters, especially phenyl esters substituted by electron-attracting substituents (obtainable, for example, by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), and also cyanomethyl esters (obtainable, for example, by treatment of the corresponding acid with chloroacetonitrile in the presence of a base; cyanomethyl esters method), thioesters, especially unsubstituted or, for example, nitro-substituted phenyl thioesters (obtainable, for example, by treatment of the corresponding acid with unsubstituted or, for example, nitro-substituted thiophenols, inter alia using the anhydride or carbodiimide method; activated thioesters method) and especially amino esters or amido esters (obtainable, for example, by treatment of the corresponding acid with an N-hydroxyamino or N-hydroxyamido compound, or with an activated derivative thereof, for example N-hydroxysuccinimide, N-hydroxypiperidine, N-hydroxyphthalimide, N-hydroxy-5-norbornene- or -norbornane-2,3-dicarboxylic acid imide, 1-hydroxybenzotriazole, a benzotriazol-1-yloxyphosphonium salt or benzotriazol-1-yluronium salt or 3-hydroxy-3,4-dihydro-1,2,3-benzotriazin-4-one, for example according to the anhydride or carbodiimide method; activated N-hydroxy esters method).

Reactive anhydrides derived from carboxy may preferably be mixed anhydrides, for example anhydrides with inorganic acids, such as acid halides, especially acid chlorides (obtainable, for example, by treatment of the corresponding acid with thionyl chloride, phosphorus pentachloride or oxalyl chloride; acid chloride method), azides (obtainable, for example, from a corresponding acid ester via the corresponding hydrazide and treatment of the latter with nitrous acid; azide method), anhydrides with carbonic acid semiesters, for example carbonic acid lower alkyl semiesters (obtainable, for example, by treatment of the corresponding acid with chloroformic acid lower alkyl esters or with a 1-lower alkoxycarbonyl-2-lower alkoxy-1,2-dihydroquinoline, for example 1-ethoxycarbonyl-2-ethoxy-1,2-dihydroquinoline; mixed O-alkylcarbonic acid anhydrides method), anhydrides with dihalogenated, especially dichlorinated, phosphoric acid (obtainable, for example, by treatment of the corresponding acid with phosphorus oxychloride; phosphorus oxychloride method), anhydrides with other phosphoric acid derivatives (for example those which can be obtained with phenyl-N-phenylphosphoramidochloridate) or anhydrides with phosphorous acid derivatives, or anhydrides with organic acids, such as mixed anhydrides with organic carboxylic acids (obtainable, for example, by treatment of the corresponding acid with an unsubstituted or substituted lower alkane- or phenyl-lower alkane-carboxylic acid halide, for example phenylacetic acid chloride, pivalic acid chloride or trifluoroacetic acid chloride; mixed carboxylic acid anhydrides method) or anhydrides with organic sulfonic acids (obtainable, for example, by treatment of a salt, such as an alkali metal salt, of the corresponding acid with a suitable organic sulfonic acid halide, such as a lower alkane- or aryl-sulfonic acid chloride, for example methane- or p-toluene-sulfonic acid chloride; mixed sulfonic acid anhydrides method), but may also be symmetrical anhydrides (obtainable, for example, by condensation of the corresponding acid in the presence of a carbodiimide or of 1-diethylaminopropyne; symmetrical anhydrides method).

Reactive cyclic amides derived from carboxy are especially amides with five-membered diazacycles of aromatic nature, such as amides with imidazoles, for example with imidazole (obtainable, for example, by treatment of the corresponding acid with N,N'-carbonyldiimidazole; imidazole method), or pyrazoles, for example with 3,5-dimethylpyrazole (obtainable, for example, via the acid hydrazide by treatment with acetyl acetone; pyrazolide method).

The condensation to produce the amide bond is carried out in a manner known per se, for example as described in standard works [for example in "Houben-Weyl-Methoden der organischen Chemie" (vol. 15/II, 4th edition, Georg Thieme Verlag, Stuttgart, 1974), in "The Peptides" (ed.: E. Gross and J. Meienhofer, vols. 1 and 2, Academic Press, London and New York, 1979/1980) or in "Principles of Peptide Synthesis" (ed.: M. Bodanszky, Springer-Verlag, Berlin, 1984)].

The condensation can be carried out in the presence of one of the customary condensation agents. Customary condensation agents are, for example, carbodiimides, for example diethyl-, dipropyl-, N-ethyl-N'-(3-dimethylaminopropyl)- or, especially, dicyclohexylcarbodiimide, or suitable carbonyl compounds, for example carbonyldiimidazole, 1,2-oxazolium compounds, for example 2-ethyl-5-phenyl-1,2-oxazolium-3'-sulfonate or 2-tert-butyl-5-methylisoxazolium perchlorate, or a suitable acylamino compound, for example 2-ethoxy-1-ethoxycarbonyl-1,2-dihydroquinoline, or activated phosphoric acid derivatives, for example diphenylphosphoryl azide, diethylphosphoryl cyanide, phenyl-N-phenylphosphoramidochloridate, bis(2-oxo-3-oxazolidinyl)phosphinic acid chloride or 1-benzotriazolyloxy-tris(dimethylamino)phosphonium hexafluorophosphate.

If desired, an organic base is added, for example a tri-lower alkylamine having voluminous radicals, for example ethyldiisopropylamine, or a heterocyclic base, for example pyridine, 4-dimethylaminopyridine or, preferably, N-methylmorpholine. The condensation of acid anhydrides with amines can be effected, for example, in the presence of inorganic carbonates, for example alkali metal carbonates or hydrogen carbonates, such as sodium or potassium carbonate or hydrogen carbonate (usually together with a sulfate).

The condensation is preferably carried out in an inert, polar, aprotic, preferably anhydrous, solvent or solvent mixture, for example in a carboxylic acid amide, for example in formamide or N,N-dimethylformamide, in a halogenated hydrocarbon, for example in dichloromethane, tetrachloromethane or chlorobenzene, in a ketone, for example in acetone, in a cyclic ether, for example in tetrahydrofuran, in an ester, for example in ethyl acetate, or in a nitrile, for example in acetonitrile, or in mixtures thereof, where appropriate at reduced or elevated temperature, for example within a temperature range of from approximately −40° C. to approximately +100° C., preferably from approximately −10° C. to approximately +50° C., and, where appropriate, under an inert gas, for example in a nitrogen atmosphere.

Reactive derivatives of a carboxy group C(=O)—$Z_2$ can also be formed in situ.

In an especially preferred embodiment for the preparation of compounds I wherein $R_2$ is carboxy, there are advantageously used those anhydrides IV in which $R_2'$ and C(=O)—$Z_2$ together form the group —C(=O)—O—C(=O)— (internal anhydrides method), for example corresponding, unsubstituted or substituted succinic or glutaric acid anhydrides.

The compounds III are obtainable in a manner analogous to known methods, for example by reacting a compound of formula IIb, or a salt thereof, in customary manner with a compound of formula

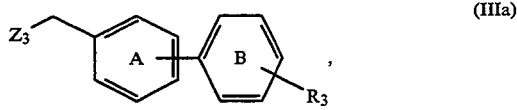

(IIIa)

wherein $Z_3$ is a nucleofugal leaving group, such as halogen, for example chlorine or bromine, hydroxy, lower alkoxy, for example methoxy or ethoxy, lower alkylthio, for example methylthio, unsubstituted or substituted amino, for example amino, N-lower alkylamino or N,N-di-lower alkylamino, or sulfonyloxy, for example optionally halogenated lower alkanesulfonyloxy or unsubstituted or substituted benzenesulfonyloxy, such as methane-, ethane-, trifluoromethane-, benzene- or p-toluene-sulfonyloxy, or with a salt thereof.

The compounds IIIa are known (cf. EP 253,310) can be prepared in a manner known per se.

A compound I obtainable in accordance with the process or by another method can be converted into a different compound I in a manner known per se.

For example, a compound I containing hydroxy can be etherified according to methods known per se. The etherification can be effected, for example, with an alcohol, such as a lower alkanol, or with a reactive ester thereof. Suitable reactive esters of the desired alcohols are, for example, those with strong inorganic or organic acids, such as corresponding halides, sulfates, lower alkanesulfonates or unsubstituted or substituted benzenesulfonates, for example chlorides, bromides, iodides or methane-, benzene- or p-toluene-sulfonates. The etherification can be effected, for example, in the presence of a base, for example an alkali metal hydride, hydroxide or carbonate, or in the presence of a basic amine. Conversely, corresponding ethers, such as lower alkoxy compounds, can be cleaved, for example by means of strong acids, such as mineral acids, for example hydrobromic or hydriodic acid, which may advantageously be in the form of pyridinium halides, or by means of Lewis acids, for example halides of elements of main group III or of the corresponding sub-groups. If necessary, these reactions may be carried out with cooling or heating, for example within a temperature range of from approximately —20° to approximately +100° C., in the presence or absence of a solvent or diluent, under an inert gas and/or under pressure and, where appropriate, in a closed vessel.

Lower alkylthio substituents can be oxidised in customary manner to corresponding lower alkane-sulfinyl or -sulfonyl. Suitable oxidising agents for the oxidation to the sulfoxide stage are, for example, inorganic peracids, such as peracids of mineral acids, for example periodic acid or persulfuric acid, organic peracids, such as percarboxylic or persulfonic acids, for example performic, peracetic, trifluoroperacetic, perbenzoic or p-toluenepersulfonic acid, or mixtures of hydrogen peroxide and acids, for example mixtures of hydrogen peroxide and acetic acid. The oxidation is frequently carried out in the presence of suitable catalysts, there being mentioned as catalysts suitable acids, such as unsubstituted or substituted carboxylic acids, for example acetic acid or trifluoroacetic acid, or transition metal oxides, such as oxides of elements of sub-group VI, for example molybdenum or tungsten oxide. The oxidation is carried out under mild conditions, for example at temperatures of from approximately —50° to approximately +100° C. The further oxidation to the sulfone stage can be carried out accordingly with dinitrogen tetroxide as catalyst in the presence of oxygen at low temperatures, as may the direct oxidation of lower alkylthio to lower alkanesulfonyl. In this case, however, the oxidising agent is usually used in excess.

If one of the variables contains amino, corresponding compounds I can be N-(ar)alkylated in a manner known per se; aminosulfonyl and carbamoyl can similarly be N-(ar)alkylated. The (ar)alkylation is effected, for example, with an (aryl)-$C_1$-$C_7$alkyl halide, for example bromide or iodide, an (aryl)-$C_1$-$C_7$alkanesulfonate, for example methanesulfonate or p-toluenesulfonate, or a di-$C_1$-$C_7$alkyl sulfate, for example dimethyl sulfate, preferably under basic conditions, such as in the presence of sodium hydroxide solution or potassium hydroxide solution, and advantageously in the presence of a phase-transfer catalyst, such as tetrabutylammonium bromide or benzyltrimethylammonium chloride, in which case, however, more strongly basic condensation agents, such as alkali metal amides, hydrides or alcoholates, for example sodium amide, sodium hydride or sodium ethanolate, may be necessary.

Amino can furthermore be acylated to acylamino in a manner known per se, for example in a manner analogous to that described under process variant b).

In compounds I that have an esterified or amidated carboxy group as substituent, such a group can be converted into the free carboxy group in customary manner, for example by means of hydrolysis, for example in the presence of a basic agent or an acidic agent, such as a mineral acid.

In an especially preferred form of the process, process variant a) can be combined with the hydrolysis of a carboxylic acid ester group $R_2$: for example, a compound II wherein $Z_1$ is cyano and $R_2$ is esterified carboxy, especially lower alkoxycarbonyl, can be converted in one step into a compound I wherein $R_2$ is carboxy and $R_3$ is 1H-tetrazol-5-yl. Corresponding advantageous procedures and reaction conditions can be gathered from the Examples.

Furthermore, in compounds I that have a carboxy group as substituent (especially if $R_3$ is other than carboxy), that group can be converted into an esterified carboxy group, for example by treatment with an alcohol, such as a lower alkanol, in the presence of a suitable esterifying agent, such as an acid reagent, for example an inorganic or organic acid or a Lewis acid, for example zinc chloride, or a water-binding condensation agent, for example a carbodiimide, such as N,N'-dicyclohexylcarbodiimide, or by treatment with a diazo reagent, such as a diazo-lower alkane, for example diazomethane. An esterified carboxy group can also be obtained by treating compounds I wherein the carboxy group is in free form or in salt form, for example in ammonium or metal salt form, for example alkali metal, such as sodium or potassium, salt form, with a $C_1$–$C_7$alkyl halide, for example methyl or ethyl bromide or iodide, or with an organic sulfonic acid ester, such as a corresponding $C_1$–$C_4$alkyl ester, for example methanesulfonic acid methyl or ethyl ester or p-toluenesulfonic acid methyl or ethyl ester.

Compounds I that have an esterified carboxy group as substituent can be converted into different ester compounds I by transesterification, for example by treatment with an alcohol, customarily with an alcohol higher than that corresponding to the esterified carboxy group in the starting material, in the presence of a suitable transesterification agent, such as a basic agent, for example an alkali metal $C_1$–$C_7$alkanoate, $C_1$–$C_7$alkanolate or cyanide, such as sodium acetate, methanolate, ethanolate, tert-butanolate or cyanide, or in the presence of a suitable acidic agent, if desired with the removal of the resulting alcohol, for example by distillation. It is also possible to use as starting material a corresponding, so-called activated, ester I that comprises an activated esterified carboxy group as substituent (see below) and to convert it into a different ester by treatment with a $C_1$–$C_7$alkanol.

It is also possible for compounds I that have the carboxy group as substituent first to be converted into a reactive derivative, such as an anhydride (also a mixed anhydride), an acid halide, for example an acid chloride (for example by treatment with a thionyl halide, for example thionyl chloride), an anhydride with a formic acid ester, for example a formic acid $C_1$–$C_7$alkyl ester (for example by treatment of a salt, such as an ammonium or alkali metal salt, with a haloformic acid ester, such as a chloroformic acid ester, such as a $C_1$–$C_7$alkyl ester), or an activated ester, such as cyanomethyl, nitrophenyl, for example 4-nitrophenyl, or polyhalophenyl, for example pentachlorophenyl, ester (for example by treatment with a corresponding hydroxy compound in the presence of a suitable condensation agent, such as N,N'-dicyclohexylcarbodiimide), and then for such a reactive derivative to be reacted with an amine, thus obtaining amide compounds I that have an amidated carboxy group as substituent. The latter can be obtained directly or via intermediates; for example, an activated ester, such as a 4-nitrophenyl ester, of a compound I having a carboxy group can first be reacted with a 1-unsubstituted imidazole, and the 1-imidazolylcarbonyl compound so obtained can be reacted with an amine. It is also possible, however, to react other, non-activated esters, such as $C_1$–$C_7$alkyl esters, of compounds I with amines.

If an aromatic ring has a hydrogen atom as substituent, the latter can be replaced by a halogen atom, in customary manner, using a halogenating agent, for example replaced by bromine using bromine, hypobromic acid, an acyl hypobromite or a different organic bromine compound, for example N-bromosuccinimide, N-bromoacetamide, N-bromophthalimide, pyridinium perbromide, dioxane dibromide, 1,3-dibromo-5,5dimethylhydantoin or 2,4,4,6-tetrabromo-2,5-cyclohexanedien-1-one, or replaced by chlorine using elemental chlorine, for example in a halogenated hydrocarbon, such as chloroform, and with cooling, for example to about $-10°$ C.

Formyl can be converted into acetalised formyl in customary manner, for example by reaction with a lower alkanol or a lower alkanediol.

If the compounds I contain unsaturated radicals, such as lower alkenyl or lower alkynyl groupings, those groupings can be converted into saturated radicals in a manner known per se. For example, the hydrogenation of multiple bonds is effected by catalytic hydrogenation in the presence of hydrogenation catalysts, there being suitable for this purpose, for example, nickels, such as Raney nickel, and noble metals and derivatives thereof, for example oxides, such as palladium or platinum oxide, which may, if desired, have been applied to carrier materials, for example carbon or calcium carbonate. The hydrogenation is preferably carried out at pressures of from approximately 1 to approximately 100 atmospheres and at temperatures of from approximately $-80°$ to approximately $+200°$ C., especially from room temperature to approximately 100° C. The reaction is advantageously effected in a solvent, such as water, a lower alkanol, for example ethanol, isopropanol or n-butanol, an ether, for example dioxane, or a lower alkanecarboxylic acid, for example acetic acid.

The invention relates especially to the processes described in the Examples.

Salts of compounds I can be prepared in a manner known per se. For example, acid addition salts of compounds I are obtained by treatment with a suitable acid or a suitable ion-exchange reagent. Salts of compounds I can be converted into the free compounds I in customary manner, acid addition salts being converted, for example, by treatment with a suitable basic agent or a suitable ion-exchange reagent.

Salts of compounds I can be converted into other salts of compounds I in a manner known per se.

Depending upon the procedure and the reaction conditions, compounds I having salt-forming properties, especially basic properties, may be obtained in free form or in the form of salts.

In view of the close relationship between the compounds I in free form and in the form of their salts, hereinbefore and hereinafter any reference to the free compounds I or their salts should be understood as including also the corresponding salts or the free compounds I, respectively, as appropriate and expedient.

The compounds I, including the salts of salt-forming compounds, may also be obtained in the form of their hydrates and/or may include other solvents, for example solvents used for crystallisation.

Depending upon the starting materials and procedures chosen, the compounds I and their salts may be in the form of one of the possible isomers or in the form of a mixture thereof, for example, depending on the number and the absolute and relative configuration of the asymmetric carbon atoms, in the form of pure isomers, such as antipodes and/or diastereoisomers, or in the form of mixtures of isomers, such as mixtures of enantiomers, for example racemates, mixtures of diastereoisomers or mixtures of racemates.

Resulting mixtures of diastereoisomers and mixtures of racemates can be separated on the basis of the physico-chemical differences between the constituents into the pure diastereoisomers or racemates in known manner, for example by fractional crystallisation. Resulting mixtures of enantiomers, such as racemates, can be separated into the optical antipodes by known methods, for example by recrystallisation from an optically active solvent, chromatography on chiral adsorbents, with the aid of suitable microorganisms, by cleavage with specific, immobilised enzymes, by the formation of inclusion compounds, for example using chiral crown ethers, in which only one enantiomer is complexed, or by conversion into diastereoisomeric salts, for example by reaction of a basic end product racemate with an optically active acid, such as carboxylic acid, for example tartaric or malic acid, or sulfonic acid, for example camphorsulfonic acid, and separation of the mixture of diastereoisomers obtained in that manner, for example on the basis of their different solubilities, into the diastereoisomers from which the desired enantiomer can be freed by the action of suitable agents. Advantageously, the more active enantiomer is isolated.

The invention relates also to those forms of the process in which a compound obtainable as intermediate at any stage of the process is used as starting material and the remaining steps are carried out, or in which a starting material is used in the form of a derivative or salt and/or its racemates or antipodes, or, especially, is formed under the reaction conditions.

The starting materials and intermediates used in the process of the present invention are preferably those which result in the compounds I described at the beginning as being especially valuable. The invention relates also to novel starting materials and intermediates for the preparation of compounds I, to their use and to a process for the preparation thereof, the variables $R_1$, $R_2$, $R_3$, p, q and X and the rings A and B being as defined for compounds I.

The compounds I and their pharmaceutically acceptable salts can be used, preferably in the form of pharmaceutically acceptable compositions, in a method for the prophylactic and/or therapeutic treatment of the animal or human body, especially as antihypertensive drugs.

The invention therefore relates also to pharmaceutical compositions that comprise as active ingredient a compound I in free form or in the form of a pharmaceutically acceptable salt, and to a process for the preparation thereof. The pharmaceutical compositions in question are for enteral, such as oral, administration and for rectal or parenteral administration to warm-blooded animals and comprise the pharmacologically active ingredient on its own or together with customary pharmaceutical excipients. The pharmaceutical compositions comprise, for example, approximately from 0.1% to 100%, preferably from approximately 1% to approximately 60%, active ingredient. Pharmaceutical compositions for enteral or parenteral administration are, for example, pharmaceutical compositions in unit dose form, such as dragées, tablets, capsules or suppositories, or also ampoules. The compositions are prepared in a manner known per se, for example by means of conventional mixing, granulating, confectioning, dissolving or lyophilising processes. For example, pharmaceutical compositions for oral administration can be obtained by combining the active ingredient with solid carriers, if desired granulating a resulting mixture and processing the mixture or granules, if desired or necessary, after the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes, using, for example, corn, wheat, rice or potato starch, gelatin, gum tragacanth, methylcellulose and/or polyvinylpyrrolidone, and, if desired, disintegrators, such as the above-mentioned starches, also carboxymethyl starch, crosslinked polyvinylpyrrolidone, agar or alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable coatings which may be enteric coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Other orally administrable pharmaceutical compositions are dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as lactose, binders, such as starches, and/or glidants, such as talc or magnesium stearate, and, where appropriate, stabilisers. In soft capsules, the active ingredient is preferably dissolved or suspended in suitable liquids, such as fatty oils, paraffin oil or liquid polyethylene glycols, to which stabilisers may also be added.

Suitable rectally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols. There may also be used gelatin rectal capsules that comprise a combination of the active ingredient with a base. Suitable bases are, for example, liquid triglycerides, polyethylene glycols and paraffin hydrocarbons.

For parenteral administration there are suitable, especially, aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that comprise viscosity-increasing substances, for example sodium carboxymethylcellulose, sorbitol and/or dextran, and, where appropriate, stabilisers.

The dose of the active ingredient may depend upon various factors, such as the method of administration, the species of warm-blooded animal, its age and/or individual condition. In normal cases, the approximate daily dose for a patient weighing about 75 kg is estimated to be, in the case of oral administration, from approximately 10 mg to approximately 250 mg.

The following Examples illustrate the invention described above without, however, implying any limitation of the scope thereof. Temperatures are given in degree Celsius.

Example 1

A solution of 8.8 g (22.7 mmol) of 3-methoxycarbonylpropanoic acid N-butyl-N-(2'-cyanobiphenyl-4-ylmethyl)-amide and 9.8 g (29.5 mmol) of tributyltin azide in 100 ml of o-xylene is heated under reflux for 20 hours. The reaction mixture is then cooled to 20° and 100 ml of 1N potassium hydroxide solution are added thereto. The reaction mixture is stirred thoroughly for 2 hours, and the aqueous phase is separated and acidified with 2N hydrochloric acid. The resin which separates is extracted with ethyl acetate. The crude product, obtained by concentration of the ethyl acetate phase by evaporation, is flash-chromatographed on 500 g of silica gel [toluene/isopropanol/glacial acetic acid (170:30:2)] to yield 3-carboxypropanoic acid N-butyl-N-[2'-(1H-tetrazol-5-yl)-biphenyl-4-ylmethyl]-amide in the form of a light-brown foam that has an $R_f$ value of 0.20 [toluene/isopropanol/glacial acetic acid (170:30:2)].

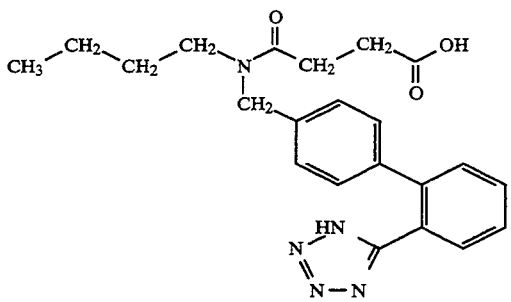

The starting material can be prepared, for example, as follows:

a) 36 ml (367 mmol) of butylamine are added to a solution of 20.0 g (73.5 mmol) of 4-bromomethyl-2'-cyano-biphenyl (cf. EP 253,310, page 159) in 150 ml dioxane and the mixture is heated under reflux for 3 hours. The reaction mixture is then concentrated by evaporation in vacuo and the residue is partitioned between 300 ml of diethyl ether and 100 ml of water. The ethereal phase is washed twice with water, dried and concentrated by evaporation. The resulting oil is flash-chromatographed on 500 g of silica gel [toluene/methanol(19:1)]. The fractions containing the product are concentrated by evaporation to yield N-butyl-N-(2'-cyanobiphenyl-4-ylmethyl)-amine in the form of a yellow oil that has an $R_f$ value of 0.34 [toluene/methanol (4:1)].

b) A solution of 5.1 g (34 mmol) of succinic acid monomethyl ester monochloride in 20 ml of ethyl acetate is added dropwise, while cooling with ice, to a solution of 6.0 g (22.7 mmol) of N-butyl-N-(2'-cyanobiphenyl-4-ylmethyl)-amine and 13 ml of Hünig base in 100 ml of ethyl acetate. The reaction mixture is stirred at from 0° to 5° for 1 hour and then 30 ml of water are added. The organic phase is washed in succession with 30 ml of 2N hydrochloric acid, water and saturated potassium hydrogen carbonate solution and is dried. Evaporation of the solvent yields crude 3-methoxycarbonyl-propanoic acid N-butyl-N-(2'-cyanobiphenyl-4-ylmethyl)-amide in the form of an oil that has an $R_f$ value of 0.32 [toluene/methanol (19:1)].

Example 2

A solution of 4.0 g (9.8 mmol) of 3-methoxycarbonyl-3-methyl-butanoic acid N-butyl-N-(2'-cyanobiphenyl-4-ylmethyl)-amide and 4.3 g (13 mmol) of tributyltin azide in 80 ml of o-xylene is reacted analogously to Example 1 for 24 hours. For hydrolysis, the reaction mixture is stirred with 50 ml of 2N potassium hydroxide solution at from 40 bis 50° for 4 hours. The aqueous phase is separated and acidified with 2N hydrochloric acid, and the oil which separates is extracted with ethyl acetate. Washing of the ethyl acetate solution with water, drying over MgSO$_4$ and concentration by evaporation yield 3-carboxy-3-methyl-butanoic acid N-butyl-N-[2'-(1H-tetrazol-5-yl)biphenyl-4-ylmethyl]-amide in the form of a colourless foam that has an $R_f$ value of 0.25 [toluene/isopropanol/glacial acetic acid (170:30:2)].

The starting material can be prepared, for example, as follows:

a) A solution of 3.6 g (13.5 mmol) of N-butyl-N-(2'-cyanobiphenyl-4-ylmethyl)-amine and 1.75 g (13.5 mmol) of 2,2-dimethylsuccinic acid anhydride in 50 ml of dioxane is heated under reflux for 5 hours. Concentration of the reaction mixture by evaporation yields crude 3-carboxy-3-methyl-butanoic acid N-butyl-N-(2'-cyanobiphenyl-4-ylmethyl)-amide that melts at from 125° to 131° and is further used in crude form.

b) A mixture of 4.8 g (12.2 mmol) of 3-carboxy-3-methyl-butanoic acid N-butyl-N-(2'-cyanobiphenyl-4-ylmethyl)-amide, 2.2 g (15.9 mmol) of potassium carbonate, 1.7 g (13.5 mmol) of dimethyl sulfate and 50 ml of N,N-dimethylformamide is stirred at an internal temperature of from 50° to 60° for from 3 to 4 hours. After cooling, the undissolved material is filtered off, the filtrate is concentrated by evaporation in vacuo and the residue is dissolved in ethyl acetate. Washing and drying of the solution and concentration thereof by evaporation in vacuo yield a crude product which is purified by flash-chromatography [toluene/methanol (75:1)]. The resulting 3-methoxycarbonyl3-methyl-butanoic acid N-butyl-N-(2'-cyanobiphenyl-4-ylmethyl)-amide is in the form of a yellowish oil that has an $R_f$ value of 0.20 [toluene/isopropanol/glacial acetic acid (170:30:2)].

Example 3

A solution of 5.5 g (11.3 mmol) of 4-methoxycarbonyl-4-methyl-pentanoic acid N-butyl-N-(2'-cyanobiphenyl-4-ylmethyl)-amide and 4.9 g (14.2 mmol) of tributyltin azide in 50 ml of o-xylene is reacted and worked up analogously to Example 2 to yield 4-carboxy-4-methyl-pentanoic acid N-butyl-N-[2'-(1H-tetrazol-5-yl)biphenyl4-ylmethyl]-amide in the form of a beige-coloured foam that has an $R_f$ value of 0.34 [toluene/isopropanol/glacial acetic acid (170:30:2)].

The starting material can be prepared, for example, as follows: A solution of 3.3 g (17 mmol) of 4-methoxycarbonyl-4-methyl-pentanoic acid chloride in 20 ml of ethyl acetate is added dropwise at from 0° to 5° to a solution of 3.0 g (11.3 mmol) of N-butyl-N-(2'-cyanobiphenyl-4-ylmethyl)-amine and 6.5 ml of Hünig base in 50 ml of ethyl acetate. The reaction mixture is stirred for 1 hour and then worked up analogously to Example 1 b) to yield 4-methoxycarbonyl-4-methyl-pentanoic acid N-butyl-N-(2'-cyano-biphenyl-4-ylmethyl)-amide in the form of an oil that has an $R_f$ value of 0.27 [toluene/methanol (19:1)] and is further used in crude form.

Example 4

A solution of 3.45 g of 3,3-dimethyl-4-methoxycarbonyl-butanoic acid N-(2'-cyanobiphenyl-4-ylmethyl)-N-propyl-amide and 11.3 g of tributyltin azide in 100 ml of xylene is heated under reflux for 3 hours. 50 ml of 2N sodium hydroxide solution are added and the mixture is stirred at 60° for 90 minutes. After cooling, the aqueous phase is acidified and extracted once with 100 ml and twice with 40 ml each time of $CH_2Cl_2$. The dichloromethane phase yields, after drying over $Na_2SO_4$ and removal of the solvents, a colourless foam. Purification of the latter by chromatography on silica gel 60 (40–63 μm) using $CH_2Cl_2/CH_3OH$ (95:5) as eluant yields pure 4-carboxy-3,3-dimethyl-butanoic acid N-propyl-N-[2'-(1H-tetrazol-5-yl)biphenyl-4-ylmethyl]-amide that has an $R_f$ value of 0.44 [$CH_2Cl_2/CH_3OH$ (4:1)].

The starting material can be prepared, for example, as follows:

a) 10.84 g of 4-bromomethyl-2'-cyano-biphenyl are mixed at room temperature with 20 ml of propylamine. The mixture is stirred for 30 minutes, during which heating to reflux temperature occurs, is then diluted with 400 ml of $CH_2Cl_2$ and washed with 200 ml of $NaHCO_3$ solution. The organic phase is dried over $Na_2SO_4$ and freed of the solvents in vacuo to leave a yellow oil. Purification of the latter by chromatography on silica gel 60 (40–63 μm) using $CH_2Cl_2/CH_3OH$ (98:2) as eluant yields pure N-(2'-cyanobiphenyl-4-ylmethyl)-N-propyl-amine that has an $R_f$ value of 0.15 [$CH_2Cl_2/CH_3OH$ (95:5)].

b) 1.83 ml of triethylamine are added to a solution of 2.19 g of N-(2'-cyanobiphenyl-4-ylmethyl)-N-propyl-amine and 2.37 g of 3,3-dimethylglutaric acid monomethyl ester monochloride in 100 ml of $CH_2Cl_2$ and the mixture is stirred at room temperature for 2 hours. Extraction twice with 50 ml of water each time and extraction of the aqueous phase with 40 ml of $CH_2Cl_2$ produces an organic phase which, after being concentrated by evaporation, yields by the customary procedure 3,3-dimethyl-4-methoxycarbonyl-butanoic acid N-(2'-cyanobiphenyl-4-ylmethyl)-N-propyl-amide that has an $R_f$ value of 0.66 [$CH_2Cl_2/CH_3OH$ (95:5)].

Example 5

A solution of 1.88 g of 4-methoxycarbonyl-4-methyl-pentanoic acid N-(2'-cyanobiphenyl-4-ylmethyl)-N-propyl-amide and 6.0 g of tributyltin azide in 50 ml of xylene is heated under reflux for 17 hours. The mixture is then concentrated by evaporation, the residue is taken up in 25 ml of 2N sodium hydroxide solution and the aqueous mixture is extracted three times with 50 ml of diethyl ether each time. The aqueous phase is acidified and washed once with 50 ml and twice with 25 ml each time of $CH_2Cl_2$. The crude product obtained from the $CH_2Cl_2$ phase by the customary procedure yields, after chromatography on silica gel 60 (40–63 μm) using $CH_2Cl_2/CH_3OH$ (95:5) as eluant, pure 4-methoxycarbonyl-4-methyl-pentanoic acid N-propyl-N-[2'-(1H-tetrazol-5-yl)biphenyl-4-ylmethyl]-amide that has an $R_f$ value of 0.59 [$CH_2Cl_2/CH_3OH$ (4:1)].

The starting material can be prepared, for example, as follows: 2.89 g of 4-methoxycarbonyl-4-methyl-pentanoic acid chloride are added to a solution of 2.50 g of N-(2'-cyanobiphenyl-4-ylmethyl)-N-propyl-amine and 2.09 ml of triethylamine in 100 ml of $CH_2Cl_2$, and the mixture is stirred for 1 hour. The reaction mixture is washed twice with 50 ml of water each time and the combined aqueous phases are extracted with 50 ml of $CH_2Cl_2$. The crude product obtained from the organic phase by the customary procedure is purified by chromatography on silica gel 60 (40–63 μm) using $CH_2Cl_2/CH_3OH$ (98:2) as eluant to yield pure 4-methoxycarbonyl-4-methyl-pentanoic acid N-(2'-cyanobiphenyl-4-ylmethyl)-N-propyl-amide that has an $R_f$ value of 0.56 [$CH_2Cl_2/CH_3OH$ (95:5)].

Example 6

A solution of 0.450 g of 4-methoxycarbonyl-4-methyl-pentanoic acid N-propyl-N-[2'-(1H-tetrazol-5-yl)biphenyl-4-ylmethyl]-amide and 2.0 ml of 2N potassium hydroxide solution in 10 ml of methanol is heated under reflux for 6 hours. When cool, the mixture is acidified and concentrated by evaporation. The residue is purified by chromatography on silica gel 60 (40–63 μm) using $CH_2Cl_2/CH_3OH$ (95:5) as eluant to yield pure 4-carboxy-4-methyl-pentanoic acid N-propyl-N-[2'-(1H-tetrazol-5-yl)biphenyl-4-ylmethyl]-amide that has an $R_f$ value of 0.40 [$CH_2Cl_2/CH_3OH$ (4:1)].

Example 7

A solution of 2.93 g of 4-carboxy-4-ethyl-hexanoic acid N-butyl-N-(2'-cyano-biphenyl-4-ylmethyl)-amide and 8.8 g of tributyltin azide in 75 ml of xylene is heated under reflux for 23 hours. When cool, the mixture is extracted with 50 ml of 2N sodium hydroxide solution. The aqueous phase is acidified and extracted once with 100 ml and twice with 30 ml each time of $CH_2Cl_2$. The combined dichloromethane phases yield, after customary treatment, a crude product that yields, after chromatography on silica gel 60 (40–63 μm) using $CH_2Cl_2/CH_3OH$ (95:5) as eluant, pure 4-carboxy-4-ethyl-hexanoic acid N-butyl-N-[2'-(1H-tetrazol-5-yl)biphenyl-4-ylmethyl]-amide that has an $R_f$ value of 0.46 [$CH_2Cl_2/CH_3OH$ (4:1)].

The starting material can be prepared, for example, as follows: A solution of 3.2 g of N-butyl-N-(2'-cyanobiphenyl-4-ylmethyl)-amine and 3.09 g of 2,2-diethylglutaric acid anhydride in 50 ml of dioxane is heated at 115° (bath temperature) for 6 hours. After concentration of the reaction mixture by evaporation, the residue is taken up in 100 ml of ethyl acetate, and the ethyl acetate phase is washed twice with 50 ml of water each time, dried over $Na_2SO_4$ and concentrated by evaporation in vacuo. Chromatography of the evaporation residue on silica gel 60 (40–63 μm) using $CH_2Cl_2/CH_3OH$ (95:5) as eluant yields pure 4-carboxy-4-ethyl-hexanoic acid N-butyl-N-(2'-cyanobiphenyl-4-ylmethyl)-amide that has an $R_f$ value of 0.72 [$CH_2Cl_2/CH_3OH$ (4:1)].

Example 8

Analogously to Example 4 and using 4.04 g of 2-ethoxycarbonylbutanoic acid N-butyl-N-(2'-cyanobiphenyl-4-ylmethyl)-amide as starting material, there is obtained, after chromatography of the crude product on silica gel 60 (40–63 μm) using $CH_2Cl_2/CH_3OH$ (9:1) as eluant, pure 2-carboxybutanoic acid N-butyl-N-[2'-(1H-tetrazol-5-yl)biphenyl-4-ylmethyl]-amide that has an $R_f$ value of 0.56 [$CH_2Cl_2/CH_3OH$ (4:1)].

The starting material can be prepared, for example, as follows: Analogously to Example 4b) and using 2.64 g of N-butyl-N-(2'-cyanobiphenyl-4-ylmethyl)-amine and 2.68 g of ethylmalonic acid monoethyl ester monochloride as starting materials, there is obtained 2-ethoxycarbonylbutanoic acid N-butyl-N-(2'-cyano-biphenyl-4-ylmethyl)-amide that has an $R_f$ value of 0.65 [$CH_2Cl_2/CH_3OH$ (95:5)].

Example 9

Analogously to Example 4 and using 4.20 g of 4-carboxy-4-ethyl-hexanoic acid N-(2'-cyanobiphenyl-4-ylmethyl)-N-propyl-amide as starting material, there is obtained, after chromatography of the crude product on silica gel 60 (40–63 μm) using $CH_2Cl_2/CH_3OH$ (95:5) as eluant, pure 4-carboxy-4-ethyl-hexanoic acid N-propyl-N-[2'-(1H-tetrazol-5-yl)biphenyl-4-ylmethyl]-amide that has an $R_f$ value of 0.58 [$CH_2Cl_2/CH_3OH$ (4:1)].

The starting material can be prepared, for example, as follows: A mixture of 2.50 g of N-(2'-cyanobiphenyl-4-ylmethyl)-N-propyl-amine 2.58 g of 2,2-diethylglutaric acid anhydride and 50 ml of dioxane is stirred under reflux for 1 hour.

After concentration of the reaction mixture by evaporation, the residue is taken up in 100 ml of ethyl acetate and the ethyl acetate phase is washed twice with 50 ml of water each time, dried over sodium sulfate and concentrated by evaporation in vacuo. The 4-carboxy-4-ethylhexanoic acid N-(2'-cyanobiphenyl-4-ylmethyl)-N-propyl-amide so obtained is further used in crude form.

Example 10

Analogously to Example 4 and using 4.19 g of 4-carboxy-3,3-tetramethylene-butanoic acid N-(2'-cyanobiphenyl-4-ylmethyl)-N-propyl-amide as starting material, there is obtained, after chromatography of the crude product on silica gel 60 (40–63 μm) using $CH_2Cl_2/CH_3OH$ (95:5) as eluant, pure 4-carboxy-3,3-tetramethylene-butanoic acid N-propyl-N-[2'-(1H-tetrazol-5-yl)biphenyl-4-ylmethyl]-amide that has an $R_f$ value of 0.48 [$CH_2Cl_2/CH_3OH$ (4:1)].

The starting material can be prepared, for example, as follows: Analogously to Example 7a), 2.50 g of N-(2'-cyanobiphenyl-4-ylmethyl)-N-propyl-amine are reacted with 2.02 g of 3,3-tetramethyleneglutaric acid anhydride. Working up by extraction yields 4-carboxy-3,3-tetramethylene-butanoic acid N-(2'-cyanobiphenyl-4-ylmethyl)-N-propyl-amid that has an $R_f$ value of 0.80 [$CH_2Cl_2/CH_3OH$ (4:1)].

Example 11

Analogously to Example 10, it is possible to obtain 4-carboxy-3,3-tetramethylene-butanoic acid N-butyl-N-[2'-(1H-tetrazol-5-yl)biphenyl-4-ylmethyl]amide that has an $R_f$ value of 0.49 [$CH_2Cl_2/CH_3OH$ (4:1)].

Example 12

Analogously to Example 10, it is possible to obtain 3-carboxy-3,3-tetramethylene-propanoic acid N-propyl-N-[2'-(1H-tetrazol-5-yl)biphenyl-4-ylmethyl]-amide that melts at from 104° to 109°.

Example 13

Analogously to Example 10, it is possible to obtain 3-carboxy-3,3-tetramethylene-propanoic acid N-butyl-N-[2'-(1H-tetrazol-5-yl)biphenyl-4-ylmethyl]amide that melts at from 122° to 127°.

Example 14

Analogously to Example 9, it is possible to obtain 3-carboxy-3-ethyl-pentanoic acid N-propyl-N-[2'-(1H-tetrazol-5-yl)biphenyl-4-ylmethyl]-amide that melts at from 105° to 114°.

Example 15

In a manner analogous to that described in one of the preceding Examples, it is also possible to obtain:

1. 4-carboxy-4,4-tetramethylene-butanoic acid N-propyl-N-[2'-(1H-tetrazol-5-yl)-biphenyl-4-ylmethyl]-amide;
2. 4-carboxy-4,4-tetramethylene-butanoic acid N-butyl-N-[2'-(1H-tetrazol-5-yl)-biphenyl-4-ylmethyl]-amide
3. 2-carboxy-2-ethyl-butanoic acid N-butyl-N-[2'-(1H-tetrazol-5-yl)biphenyl-4-ylmethyl]-amide;
4. 2-carboxy-2-ethyl-butanoic acid N-propyl-N-[2'-(1H-tetrazol-5-yl)biphenyl-4-ylmethyl]-amide;
5. 2-carboxybutanoic acid N-propyl-N-[2'-(1H-tetrazol-5-yl)biphenyl-4-ylmethyl]-amide;
6. 3-carboxy-3-ethyl-pentanoic acid N-butyl-N-[2'-(1H-tetrazol-5-yl)biphenyl-4-ylmethyl]-amide;
7. 3-carboxy-3,3-pentamethylene-propanoic acid N-propyl-N-[2'-(1H-tetrazol-5-yl)-biphenyl-4-ylmethyl]-amide;
8. 3-carboxy-3,3-pentamethylene-propanoic acid N-butyl-N-[2'-(1H-tetrazol-5-yl)-biphenyl-4-ylmethyl]-amide;
9. 5-carboxy-5,5-tetramethylene-pentanoic acid N-propyl-N-[2'-(1H-tetrazol-5-yl)-biphenyl-4-ylmethyl]-amide;
10. 5-carboxy-5,5-tetramethylene-pentanoic acid N-butyl-N-[2'-(1H-tetrazol-5-yl)-biphenyl-4-ylmethyl]-amide;
11. 3-carboxy-2,2-tetramethylene-propanoic acid N-propyl-N-[2'-(1H-tetrazol-5-yl)-biphenyl-4-ylmethyl]-amide;
12. 3-carboxy-2,2-tetramethylene-propanoic acid N-butyl-N-[2'-(1H-tetrazol-5-yl)-biphenyl-4-ylmethyl]-amide;
13. 2,2-pentamethylene-2-trifluoromethanesulfonylamino-ethanoic acid N-butyl-N-[2'-(1H-tetrazol-5-yl)biphenyl-4-ylmethyl]-amide; and
14. 2,2-pentamethylene-2-trifluoromethanesulfonylamino-ethanoic acid N-propyl-N-[2'-(1H-tetrazol-5-yl)biphenyl-4-ylmethyl]-amide.

Example 16

A solution of 2.58 g of 4-carboxy-4,4-pentamethylene-butanoic acid N-propyl-N-(2'-cyanobiphenyl-4-ylmethyl)-amide and 8.0 g of tributyltin azide in 60 ml of xylene is heated under reflux for 16 hours. When cool, the reaction mixture is stirred with 30 ml of 2N sodium hydroxide solution for 30 minutes. The aqueous phase is extracted three times with 50 ml of ether and is then acidified and extracted three times with 50 ml of $CH_2Cl_2$. After customary treatment, the combined dichloromethane phases yield a crude product that yields, after chromatography on silica gel 60 (40–63 μm) using $CH_2Cl_2/CH_3OH$ (95:5) as eluant, 4-carboxy-4,4-pentamethylene-butanoic acid N-propyl-N-[2'-(1H-tetrazol-5-yl)-biphenyl-4-ylmethyl]-amide that has an $R_f$ value of 0.48 [$CH_2Cl_2/CH_3OH$ (4:1)].

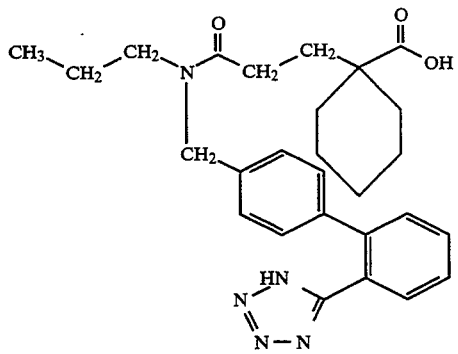

The starting material can be prepared, for example, as follows:

A solution of 1.37 g of N-(2'-cyanobiphenyl-4-ylmethyl)-N-propyl-amine and 1.20 g of 2-oxaspiro[5.5]undecane-1,3-dione in 30 ml of dioxane is heated under reflux for 3 hours. After removal of the solvent, the residue is taken up in 50 ml of ethyl acetate and washed twice with 25 ml of water. After being dried and concentrated by evaporation, the organic phase yields 4-carboxy-4,4-pentamethylene-butanoic acid N-propyl-N-(2'-cyano-biphenyl-4-ylmethyl)-amide.

Example 17

Analogously to Example 16 and using 2.63 g of 4-carboxy-4,4-penta-methylene-butanoic acid N-butyl-N-(2'-cyanobiphenyl-4-ylmethyl)-amide and 7.80 g of tributyltin azide as starting materials, there is obtained, after chromatography on silica gel 60 (40–63 μm) using $CH_2Cl_2/CH_3OH$ (95:5) as eluant, 4-carboxy-4,4-pentamethylene-butanoic acid N-butyl-N-[2'-(1H-tetrazol-5-yl)-biphenyl-4-ylmethyl]-amide that has an $R_f$ value of 0.32 [$CH_2Cl_2/CH_3OH$ (4:1)].

The starting material can be prepared, for example, as follows: Analogously to Example 16, 1.35 g of N-butyl-N-(2'-cyanophenyl-4-ylmethyl)-amine are reacted with 1.20 g of 2-oxaspiro[5.5]undecane-1,3-dione to form 4-carboxy-4,4-penta-methylene-butanoic acid N-butyl-N-(2'-cyanobiphenyl-4-ylmethyl)-amide. Example 18

A solution of 2.76 g of N-(2'-cyanobiphenyl-4-ylmethyl)-N-propyl-isophthalic acid monoamide and 8.68 g of tributyltin azide in 75 ml of xylene is heated under reflux for 2 hours. When cool, the mixture is stirred with 50 ml of 2N sodium hydroxide solution at room temperature for 1 hour, and is then acidified and extracted with 100 ml and twice with 50 ml of $CH_2Cl_2$. After customary treatment, the combined dichloromethane phases yield a crude product that, after chromatography on silica gel 60 (40–63 μm) using $CH_2Cl_2/CH_3OH$ (9:1) as eluant, yields N-propyl-N-[2'-(1H-tetrazol-5-yl)-biphenyl-4-ylmethyl]-isophthalic acid monoamide that has an $R_f$ value of 0.10 [$CH_2Cl_2/CH_3OH$ (4:1)].

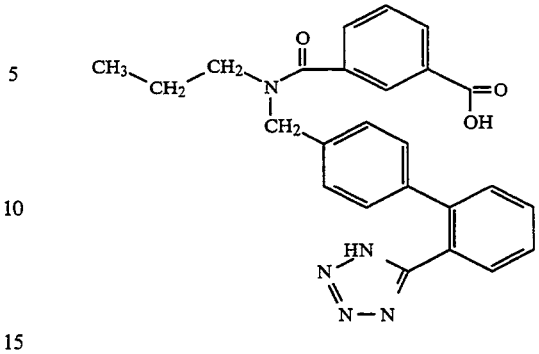

The starting material can be prepared, for example, as follows:

A solution of 2.50 g of N-(2'-cyanobiphenyl-4-ylmethyl)-N-propyl-amine, 2.98 g of isophthalic acid monomethyl ester monochloride and 2.10 ml of triethylamine in 100 ml of $CH_2Cl_2$ is stirred at room temperature for 1 hour. Extraction twice with 50 ml of water each time and customary treatment of the organic phase yields a crude product that, after chromatography on silica gel 60 (40–63 μm) using $CH_2Cl_2$ as eluant, yields N-(2'-cyanobiphenyl-4-ylmethyl)-N-propyl-isophthalic acid monoamide that has an $R_f$ value of 0.61 [$CH_2Cl_2/CH_3OH$ (4:1)].

Example 19

A solution of 2.50 g of 2-carboxy-phenylacetic acid N-butyl-N-(2'-cyanobiphenyl-4-ylmethyl)-amide and 6.50 g of tributyltin azide in 50 ml of xylene is heated under reflux for 15 hours. When cool, the mixture is stirred with 50 ml of 2N sodium hydroxide solution at room temperature for 30 minutes. The aqueous phase is acidified and extracted three times with 50 ml of $CH_2C_2$ each time. After customary treatment, the combined dichloromethane phases yield a crude product that, after chromatography on silica gel 60 (40–63 μm) using $CH_2Cl_2/CH_3OH$ (97:3)) as eluant, yields 2-carboxy-phenylacetic acid N-butyl-N-[2'-(1H-tetrazol-5-yl)-biphenyl-4-ylmethyl]-amide that has an $R_f$ value of 0.37 [$CH_2Cl_2/CH_3OH$ (4:1)].

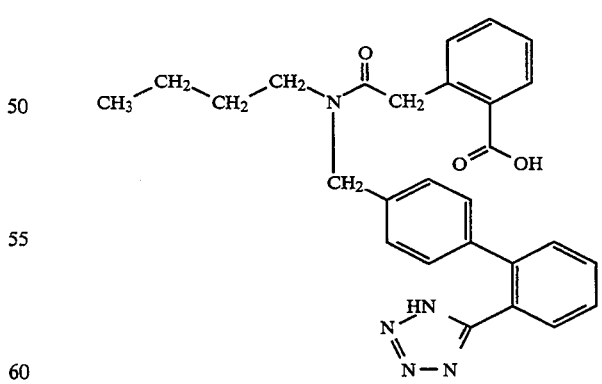

The starting material can be prepared, for example, as follows: A solution of 2.64 g of N-butyl-N-(2'-cyanobiphenyl-4-ylmethyl)-amine and 2.43 g of homophthalic acid anhydride in 50 ml of dioxane is heated under reflux for hour. After removal of the solvent, the residue is taken up in 100 ml of ethyl acetate and washed twice with 50 ml of water each time. After customary treatment, the organic phase yields a crude product that yields, from CH₂Cl₂/ether/hexane, 2-carboxy-phenylacetic acid N-butyl-N-(2'-cyanobiphenyl-4-ylmethyl)-amide, m.p. 137°-139°.

Example 20

N-butyl-3-methyl-N-[2'-(1H-tetrazol-5-yl)biphenyl-4-ylmethyl]-2-(S)-trifluoromethanesulfonylaminobutanoic acid amide Analogously to Example 1, there is obtained from 1.7 g (3.5 mmol) of N-butyl-N-(2'-cyanobiphenyl-4-ylmethyl)-3-methyl-2-(S)-trifluoromethane-sulfonylaminobutanoic acid amide a crude product which is flash-chromatographed on 150 g of silica gel (eluants ethyl acetate/ethanol/conc. ammonia (6:3:1)). The fractions containing the product ($R_f$ value 0.22) are combined and concentrated by evaporation in vacuo. The evaporation residue is partitioned between ethyl acetate and 1N hydrochloric acid. The organic phase is separated, washed with brine, dried and concentrated by evaporation to yield the title compound in the form of a beige foam (FAB-MS MH⁺=539).

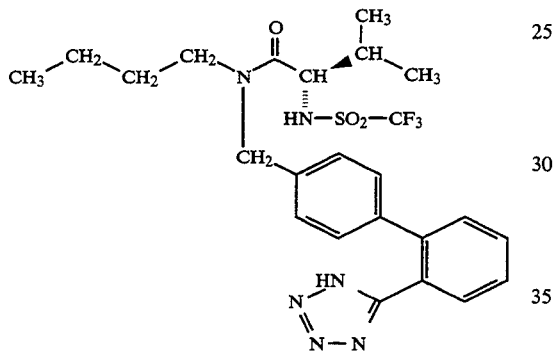

The starting material can be prepared, for example, as follows: Analogously to Example 21c) and using 1.3 g (3.5 mmol) of 2-(S)-amino-N-butyl-N-(2'-cyanobiphenyl-4-ylmethyl)-3-methyl-butanoic acid amide, 1.0 ml (5.8 mmol) of Hünig base and 1.3 g (4.6 mmol) of trifluoromethanesulfonic acid anhydride, N-butyl-N-(2'-cyanobiphenyl-4-ylmethyl)-3-methyl-2-(S)-trifluoromethanesulfonyl-amino-butanoic acid amide is obtained in the form of a crude oil that is used in the next step without being further purified.

Example 21

2-(S)-methanesulfonylamino-3-methyl-butanoic acid N-butyl-N-[2'-(1H-tetrazol-5-yl)biphenyl-4-ylmethyl]-amide Analogously to Example 20 and using 2.2 g (5 mmol) of 2-(S)-methanesulfonylamino-3-methylbutanoic acid N-butyl-N-(2'-cyanobiphenyl-4-ylmethyl)amide and 2.5 g (7.5 mmol) of tributyltin azide, the title compound is obtained in the form of a light-coloured foam that has an $R_f$ value of 0.45 [toluene/isopropanol/glacial acetic acid (170:30:2)].

The starting material can be prepared, for example, as follows:

a) A solution of 2.17 g (10 mmol) of BOC-L-valine and 1.1 ml (10 mmol) of N-methylmorpholine in 20 ml of dichloromethane is cooled to −5°. 1.23 ml (10 mmol) of pivalic acid chloride is added dropwise at −5° with stirring. The solution is stirred at 0° for 2 hours, and a solution of 2.64 g (10 mmol) of N-butyl-N-(2'-cyanobiphenyl-4-ylmethyl)-amine in 10 ml of dichloromethane is then added dropwise thereto. The reaction mixture is subsequently stirred at room temperature for 24 hours. It is then diluted with 30 ml of dichloromethane, washed in succession with 1N hydrochloric acid (20 ml), saturated potassium bicarbonate solution (10 ml) and water, dried and concentrated in vacuo to yield crude N-butyl-N-[2'-cyanobiphenyl-4-ylmethyl]-2-[(S)-tert-butoxycarbonylamino]-3-methyl-butanoic acid amide in the form of a low-melting-point mass.

b) 4.7 g (10 mmol) of crude N-butyl-N-[2'-cyanobiphenyl-4-ylmethyl]-2-[(S)-tert-butoxycarbonylamino]-3-methyl-butanoic acid amide are dissolved in a mixture of 30 ml of formic acid and 10 ml of dioxane and the solution is left to stand at room temperature for 20 hours. After concentration of the solution by evaporation in vacuo, the residue is partitioned between ethyl acetate and 2N sodium hydroxide solution, and the organic phase is separated, washed with brine, dried and concentrated by evaporation to yield 2-(S)-amino-N-butyl-N-(2'-cyanobiphenyl-4-ylmethyl)-3-methyl-butanoic acid amide in the form of a yellowish oil that can be used without being further purified.

c) A solution of 0.75 g (6.5 mmol) of methanesulfonic acid chloride in 5 ml of dichloromethane is added dropwise, with stirring, to a solution of 1.8 g (5 mmol) of 2-(S)-amino-N-butyl-N-(2'-cyanobiphenyl-4-ylmethyl)-3-methyl-butanoic acid amide and 1.4 ml (8 mmol) of Hünig base in 10 ml of dichloromethane. The reaction mixture is stirred at room temperature for a further 5 hours, diluted with 50 ml of dichloromethane and extracted with 20 ml of 4N hydrochloric acid. The dichloromethane phase is separated, washed in succession with water, 10 ml of bicarbonate solution and brine, dried and concentrated by evaporation to yield crude N-butyl-N-(2'-cyanobiphenyl-4-ylmethyl)-2-(S)-methanesulfonylamino-3-methylbutanoic acid amide in the form of a yellowish oil of $R_f$ value 0.56 [toluene/isopropanol/glacial acetic acid (170:30:2)]that can be used in the next step without being further purified.

Example 22

Tablets, each comprising 50 mg of active ingredient, for example 4-carboxy-4-methyl-pentanoic acid N-propyl-N-[2'-(1H-tetrazol-5-yl)biphenyl-4-ylmethyl]-amide, can be prepared as follows:

| Composition (for 10 000 tablets): | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silica (highly dispersed) | 20.0 g |
| ethanol | q.s. |

The active ingredient is mixed with the lactose and 292 g of the potato starch, and the mixture is moistened with an alcoholic solution of the gelatin and granulated through a sieve. After drying, the remainder of the potato starch, the talc, the magnesium stearate and the highly dispersed silica are mixed in and the mixture is compressed to form tablets which each weigh 145.0 mg and comprise 50.0 mg of active ingredient, and which may, if desired, be provided with breaking notches for finer adaptation of the dose.

Example 23

Film-coated tablets, each comprising 100 mg of active ingredient, for example 4-carboxy-4-methyl-pentanoic acid N-propyl-N-[2'-(1H-tetrazol-5-yl)biphenyl-4-ylmethyl]-amide, can be prepared as follows:

| Composition (for 1000 tablets): | |
| --- | --- |
| active ingredient | 100.00 g |
| lactose | 100.00 g |
| corn starch | 70.00 g |
| talc | 8.50 g |
| calcium stearate | 1.50 g |
| hydroxypropylmethylcellulose | 2.36 g |
| shellac | 0.64 g |
| water | q.s. |
| dichloromethane | q.s. |

The active ingredient, the lactose and 40 g of the corn starch are mixed, and the mixture is moistened with a paste, prepared from 15 g of the corn starch and water (with heating), and granulated. The granules are dried, the remainder of the corn starch, the talc and the calcium stearate are added and mixed with the granules. The mixture is compressed to form tablets (weight: 280 mg) which are film-coated with a solution of the hydroxypropylmethylcellulose and the shellac in dichloromethane (final weight of a film-coated tablet: 283 mg).

Example 24

In a manner analogous to that described in Examples 22 and 23, it is also possible to prepare tablets and film-coated tablets comprising a different compound I or a pharmaceutically acceptable salt of a compound I, for example according to any one of Examples 1 to 21.

What is claimed is:

1. A compound of formula

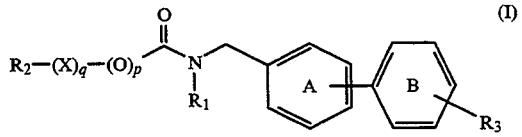

(I)

wherein $R_1$ is lower alkyl, lower alkenyl, lower alkynyl, halo-lower alkyl, -lower alkenyl or -lower alkynyl carrying halogen in a position higher than the $\beta$-position with respect to the nitrogen atom shown in formula I, hydroxy-lower alkyl, -lower alkenyl or -lower alkynyl carrying hydroxy in a position higher than the $\beta$-position with respect to the nitrogen atom shown in formula I, cyclo-lower alkyl, cyclo-lower alkenyl, phenyl-lower alkyl or phenyl-lower alkenyl or -lower alkynyl; $R_2$ is 1H-tetrazol-5-yl, carboxy, carboxy esterified by an alcohol the alcoholic hydroxy function of which is bonded to lower alkyl, lower alkenyl or lower alkynyl or to lower alkoxy-lower alkyl, -lower alkenyl or -lower alkynyl, or is carbamoyl in which the amino group is unsubstituted or is mono- or di-substituted by a substituent or substituents selected from the group consisting of lower alkyl, lower alkenyl, lower alkynyl and phenyl-lower alkyl, -lower alkenyl and -lower alkynyl, or is di-substituted by lower alkylene or by lower alkyleneoxy-lower alkylene, or is amino, amino that is mono- or di-substituted by a substituent or substituents selected from the group consisting of lower alkyl, lower alkenyl, lower alkynyl and phenyl-lower alkyl, -lower alkenyl and -lower alkynyl, or is di-substituted by lower alkylene or by lower alkyleneoxy-lower alkylene, or amino that is mono-substituted by lower alkanoyl or by benzoyl, or is formyl, di-lower alkoxymethyl, 1,3-dioxacycloalk-2-yl, hydroxy, lower alkoxy, lower alkenyloxy, phenoxy, benzyloxy, $S(O)_m$—R, wherein m is 0, 1 or 2 and R is hydrogen, lower alkyl, lower alkenyl or lower alkynyl, or lower alkanoyl, aminosulfonyl, aminosulfonyl in which the amino group is mono- or di-substituted by a substituent or substituents selected from the group consisting of lower alkyl, lower alkenyl, lower alkynyl and phenyl-lower alkyl, -lower alkenyl and -lower alkynyl, or is di-substituted by lower alkylene or by lower alkyleneoxy-lower alkylene, or $PO_2H_2$, $PO_3H_2$ or sulfonylamino in which the sulfur atom of the sulfonylamino group is mono-substituted by lower alkyl, lower alkenyl, lower alkynyl, halo-lower alkyl, -lower alkenyl or -lower alkynyl, phenyl-lower alkyl, -lower alkenyl or -lower alkynyl or by phenyl; $R_3$ is carboxy, 1H-tetrazol-5-yl, $SO_3H$, $PO_2H_2$, $PO_3H_2$ or halo-lower alkanesulfonylamino; X is straight-chained lower alkylene, straight-chained lower alkylene in which one or, independently of each other, two methylene group(s) has(have) been replaced by cyclo-lower alk-1,1-ylene, straight-chained lower alkylene that is mono-, di-, tri- or tetra-substituted by a substituent or substituents selected from the group consisting of lower alkyl, lower alkenyl and lower alkynyl, or straight-chained lower alkylene that is mono-, di-, tri- or tetra-substituted by a substituent or substituents selected from the group consisting of lower alkyl, lower alkenyl and lower alkynyl and in which one or, independently of each other, two methylene group(s) of the methylene groups present in the corresponding unsubstituted straight-chained lower alkylene group has(have) been replaced by cyclo-lower alk-1,1-ylene; each of the rings A and B, independently of the other, is unsubstituted or is substituted by halogen, hydroxy, lower alkoxy, lower alkenyloxy, phenoxy, benzyloxy, $S(O)_m$—R, wherein m is 0, 1 or 2 and R is hydrogen, lower alkyl, lower alkenyl or lower alkynyl, or by lower alkyl, lower alkenyl, lower alkynyl, halo-lower alkyl, -lower alkenyl or -lower alkynyl, hydroxy-lower alkyl, -lower alkenyl or -lower alkynyl, or by unsubstituted or halo- or hydroxy-substituted lower alkoxy-lower alkyl, -lower alkenyl or -lower alkynyl, or unsubstituted or halo- or hydroxy-substituted lower alkenyloxy-lower alkyl, -lower alkenyl or -lower alkynyl; and either p and q are both 1 or p is 0 and q is 0 or 1; wherein phenyl in phenyl radicals per se and in phenyl-lower alkyl, phenyl-lower alkenyl, phenyl-lower alkynyl, benzoyl, phenoxy and benzyloxy groups is in each case unsubstituted phenyl or phenyl mono- or poly-substituted by a substituent or substituents selected from the group consisting of halogen, hydroxy, lower alkoxy, lower alkyl and trifluoromethyl; or a pharmaceutically acceptable salt thereof.

2. A compound according to claim 1 of formula I wherein $R_1$ is lower alkyl, lower alkenyl or cyclo-lower alkyl; $R_2$ is 1H-tetrazol-5-yl, carboxy, carboxy esterified by an alcohol the alcoholic hydroxy function of which is bonded to lower alkyl, lower alkenyl or lower alkynyl or to lower alkoxy-lower alkyl, -lower alkenyl or -lower alkynyl, or is carbamoyl in which the amino group is unsubstituted or is mono- or di-substituted by a substituent or substituents selected from the group consisting of lower alkyl, lower alkenyl, lower alkynyl and phenyl-lower alkyl, -lower alkenyl and -lower alkynyl, or is di-substituted by lower alkylene or by lower alkyleneoxy-lower alkylene, or is amino, amino that is mono-or di-substituted by a substituent or substituents selected from the group consisting of lower alkyl, lower alkenyl, lower alkynyl and phenyl-lower alkyl, -lower alkenyl and -lower alkynyl, or is di-substituted by lower alkylene or by lower alkyleneoxy-lower alkylene, or amino that is mono-substituted by lower alkanoyl or by benzoyl, or is formyl, di-lower alkoxymethyl, 1,3-dioxacycloalk-2-yl, hydroxy, lower alkoxy, lower alkenyloxy, phenoxy, benzyloxy, $S(O)_m$—R, wherein m is 0, 1 or 2 and R is hydrogen, lower alkyl, lower alkenyl or lower alkynyl, or lower alkanoyl, aminosulfonyl, aminosulfonyl in which the amino group is mono- or di-substituted by a substituent or substituents selected from the group consisting of lower alkyl, lower alkenyl, lower alkynyl and phenyl-lower alkyl, -lower alkenyl and -lower alkynyl, or is di-substituted by lower alkylene or by lower alkyleneoxy-lower alkylene, or $PO_2H_2$, $PO_3H_2$ or sulfonylamino in which the sulfur atom of the sulfonylamino group is mono-substituted by lower alkyl, lower alkenyl, lower alkynyl, halo-lower alkyl, -lower alkenyl or -lower alkynyl, phenyl-lower alkyl, -lower alkenyl or -lower alkynyl or by phenyl; $R_3$ is halo-lower alkanesulfonylamino, carboxy or 1H-tetrazol-5-yl; X is straight-chained lower alkylene, straight-chained lower alkylene in which one methylene group has been replaced by cyclo-lower alk-1,1-ylene, straight-chained lower alkylene that is mono-, di-, tri- or tetra-substituted by a substituent or substituents selected from the group consisting of lower alkyl, lower alkenyl and lower alkynyl, or straight-chained lower alkylene that is mono- or di-substituted by a substituent or substituents selected from the group consisting of lower alkyl, lower alkenyl and lower alkynyl and in which one methylene group of the methylene groups present in the corresponding unsubstituted straight-chained lower alkylene group has been replaced by cyclo-lower alk-1,1-ylene; each of the rings A and B, independently of the other, is unsubstituted or is substituted by halogen, hydroxy, lower alkoxy, $S(O)_m$—R, wherein m is 0, 1 or 2 and R is hydrogen or lower alkyl, or by lower alkyl, halo-lower alkyl, hydroxy-lower alkyl, unsubstituted or halo- or hydroxy-substituted lower alkoxy-lower alkyl or by unsubstituted or halo- or hydroxy-substituted lower alkenyloxy-lower alkyl; and either p and q are both 1 or p is 0 and q is 0 or 1; wherein phenyl in phenyl radicals per se and in phenyl-lower alkyl, phenyl-lower alkenyl, phenyl-lower alkynyl, benzoyl, phenoxy and benzyloxy groups is in each case unsubstituted phenyl or phenyl mono- or di-substituted by a substituent or substituents selected from the group consisting of halogen, hydroxy, lower alkoxy, lower alkyl and trifluoromethyl; or a pharmaceutically acceptable salt thereof.

3. A compound according to claim 1 of formula I wherein $R_1$ is lower alkyl or lower alkenyl; $R_2$ is 1H-tetrazol-5-yl, carboxy, carboxy esterified by an alcohol the alcoholic hydroxy function of which is bonded to lower alkyl or to lower alkoxy-lower alkyl, or is carbamoyl in which the amino group is unsubstituted or is mono- or di-substituted by a substituent or substituents selected from the group consisting of lower alkyl and phenyl-lower alkyl, or is di-substituted by lower alkylene or by lower alkyleneoxy-lower alkylene, or is amino, amino that is mono- or di-substituted by a substituent or substituents selected from the group consisting of lower alkyl and phenyl-lower alkyl, or is di-substituted by lower alkylene or by lower alkyleneoxy-lower alkylene, or amino that is mono-substituted by lower alkanoyl, or is hydroxy, lower alkoxy, phenoxy, benzyloxy, $S(O)_m$—R, wherein m is 0, 1 or 2 and R is hydrogen or lower alkyl, or lower alkanoyl, aminosulfonyl, $PO_2H_2$, $PO_3H_2$ or sulfonylamino in which the sulfur atom of the sulfonylamino group is mono-substituted by lower alkyl, halo-lower alkyl, phenyl-lower alkyl or by phenyl; $R_3$ is carboxy or 1H-tetrazol-5-yl; X is straight-chained lower alkylene, straight-chained lower alkylene in which one methylene group has been replaced by cyclo-lower alk-1,1-ylene, or straight-chained lower alkylene that is mono-substituted by a lower alkyl substituent or di-substituted by identical or different lower alkyl substituents; each of the rings A and B, independently of the other, is unsubstituted or is substituted by halogen, hydroxy, lower alkoxy, $S(O)_m$—R, wherein m is 0, 1 or 2 and R is hydrogen or lower alkyl, or by lower alkyl; p is 0, q is 0 or 1; and the ring B is bonded in the 4-position of the ring A; wherein phenyl in phenyl-lower alkyl, phenoxy and benzyloxy groups is in each case unsubstituted phenyl or phenyl mono-substituted by a substituent selected from the group consisting of halogen, lower alkoxy, lower alkyl and trifluoromethyl; or a pharmaceutically acceptable salt thereof.

4. A compound according to claim 1 of formula I wherein X is the structural element of the formula —$X_1$—Ph—$X_2$—, wherein each of $X_1$ and $X_2$, independently of the other, is a bond or $C_1$–$C_7$alkylene and Ph is phenylene; wherein phenylene is unsubstituted phenylene or phenylene mono-substituted by a substituent selected from the group consisting of halogen, lower alkoxy, lower alkyl and trifluoromethyl; or a pharmaceutically acceptable salt thereof.

5. A compound according to claim 1 of formula I wherein the ring B is bonded in the 4-position of the ring A; wherein phenyl in phenyl-lower alkyl, phenoxy and benzyloxy groups is in each case unsubstituted phenyl or phenyl mono-substituted by a substituent selected from the group consisting of halogen, lower alkoxy, lower alkyl and trifluoromethyl; or a pharmaceutically acceptable salt thereof.

6. A compound according to claim 1 of formula I wherein $R_1$ is $C_1$–$C_4$alkyl or $C_3$–$C_5$-alkenyl; $R_2$ is 1H-tetrazol-5-yl, carboxy, $C_1$–$C_4$alkoxycarbonyl, carbamoyl, N-$C_1$–$C_4$alkylcarbamoyl, N,N-di-$C_1$–$C_4$alkylcarbamoyl, $C_1$–$C_4$alkanoyl, aminosulfonyl or sulfonylamino in which the sulfur atom of the sulfonylamino group is mono-substituted by $C_1$–$C_4$alkyl; $R_3$ is carboxy or 1H-tetrazol-5-yl; X is straight-chained $C_1$–$C_7$alkylene in which one methylene group has been replaced by $C_3$–$C_7$cycloalk-1,1-ylene, or is straight-chained $C_1$–$C_7$alkylene that is mono-substituted by a $C_1$–$C_4$alkyl substituent or di-substituted by identical or different $C_1$–$C_4$alkyl substituents; the rings A and B are unsubstituted; p is 0; q is 1; the ring B is bonded in the 4-position of the ring A; and $R_3$ is bonded in a 2-position of the ring B; or a pharmaceutically acceptable salt thereof.

7. A compound according to claim 1 of formula I wherein $R_1$ is $C_1$–$C_4$alkyl or $C_3$–$C_5$-alkenyl; $R_2$ is 1H-tetrazol-5-yl, carboxy, $C_1$–$C_4$alkoxycarbonyl, carbamoyl, N-$C_1$–$C_4$alkylcarbamoyl, N,N-di-$C_1$–$C_4$alkylcarbamoyl, $C_1$–$C_4$alkanoyl, aminosulfonyl or sulfonylamino in which the sulfur atom of the sulfonylamino group is mono-substituted by $C_1$–$C_4$alkyl; $R_3$ is carboxy or 1H-tetrazol-5-yl; X is the structural element of the formula —$X_1$—Ph—$X_2$—, wherein each of $X_1$ and $X_2$, independently of the other, is a bond or $C_1$–$C_3$alkylene and Ph is phenylene; the rings A and B are unsubstituted; p is 0, q is 1; the ring B is bonded in the 4-position of the ring A; and $R_3$ is bonded in a 2-position of the ring B; or a pharmaceutically acceptable salt thereof.

8. A compound according to claim 1 of formula I wherein $R_1$ is $C_1$–$C_4$alkyl, $R_2$ is carboxy, $C_1$–$C_4$alkoxycarbonyl or carbamoyl, $R_3$ is 1H-tetrazol-5-yl, X is straight-chained $C_1$–$C_7$alkylene in which one methylene group has been replaced by $C_3$–$C_7$cycloalk-1,1-ylene, or is straight-chained $C_1$–$C_7$alkylene that is mono-substituted by a $C_1$–$C_4$alkyl substituent or di-substituted by identical or different $C_1$–$C_4$alkyl substituents; the rings A and B are unsubstituted; p is 0; q is 1; the ring B is bonded in the 4-position of the ring A; and $R_3$ is bonded in a 2-position of the ring B; or a pharmaceutically acceptable salt thereof.

9. A compound according to claim 1 of formula I wherein $R_1$ is $C_1$–$C_4$alkyl, $R_2$ is carboxy, $R_3$ is 1H-tetrazol-5-yl, X is straight-chained $C_1$–$C_7$alkylene in which one methylene group has been replaced by $C_3$–$C_7$cycloalk-1,1-ylene, or is straight-chained $C_1$–$C_7$alkylene that is mono-substituted by a $C_1$–$C_4$alkyl substituent or di-substituted by identical or different $C_1$–$C_4$alkyl substituents; the rings A and B are unsubstituted; p is 0; q is 1; the ring B is bonded in the 4-position of the ring A; and $R_3$ is bonded in a 2-position of the ring B; or a pharmaceutically acceptable salt thereof.

10. A compound according to claim 1 of formula I wherein $R_1$ is $C_3$–$C_4$alkyl; $R_2$ is carboxy; $R_3$ is 1H-tetrazol-5-yl; X is 2-methylbut-1,3-ylene or is 1,3-propylene in which the $\omega$-methylene group has been replaced by cyclohex-1,1-ylene; the rings A and B are unsubstituted; p is 0; q is 1; the ring B is bonded in the 4-position of the ring A; and $R_3$ is bonded in a 2-position of the ring B; or a pharmaceutically acceptable salt thereof.

11. A compound selected from
3-carboxypropanoic acid N-butyl-N-[2'-(1H-tetrazol-5-yl)biphenyl-4-ylmethyl]-amide;
3-carboxy-3-methyl-butanoic acid N-butyl-N-[2'-(1H-tetrazol-5-yl)biphenyl-4-ylmethyl]-amide;
4-carboxy-4-methyl-pentanoic acid N-butyl-N-[2'-(1H-tetrazol-5-yl)biphenyl-4-ylmethyl]-amide;
4-carboxy-3,3-dimethyl-butanoic acid N-propyl-N-[2'-(1H-tetrazol-5-yl)biphenyl-4-ylmethyl]-amide;
4-methoxycarbonyl-4-methyl-pentanoic acid N-propyl-N-[2'-(1H-tetrazol-5-yl)biphenyl-4-ylmethyl]-amide;
4-carboxy-4-methyl-pentanoic acid N-propyl-N-[2'-(1H-tetrazol-5-yl)biphenyl-4-ylmethyl]-amide:
4-carboxy-4-ethyl-hexanoic acid N-butyl-N-[2'-(1H-tetrazol-5-yl)biphenyl-4-ylmethyl]-amide;
2-carboxybutanoic acid N-butyl-N-[2'-(1H-tetrazol-5-yl)biphenyl-4-ylmethyl]-amide;
4-carboxy-4-ethyl-hexanoic acid N-propyl-N-[2'-(1H-tetrazol-5-yl)biphenyl-4-ylmethyl]-amide;
4-carboxy-3,3-tetramethylene-butanoic acid N-propyl-N-[2'-(1H-tetrazol-5-yl)biphenyl-4-ylmethyl]-amide;
4-carboxy-3,3-tetramethylene-butanoic acid N-butyl-N-[2'-(1H-tetrazol-5-yl)biphenyl-4-ylmethyl]-amide;
3-carboxy-3,3-tetramethylene-propanoic acid N-propyl-N-[2'-(1H-tetrazol-5-yl)biphenyl-4-ylmethyl]-amide;
3-carboxy-3,3-tetramethylene-propanoic acid N-butyl-N-[2'-(1H-tetrazol-5-yl)biphenyl-4-ylmethyl]-amide;
3-carboxy-3-ethyl-pentanoic acid N-propyl-N-[2'-(1H-tetrazol-5-yl)biphenyl-4-ylmethyl]-amide;
4-carboxy-4,4-tetramethylene-butanoic acid N-propyl-N-[2'-(1H-tetrazol-5-yl)biphenyl-4-ylmethyl]-amide;
4-carboxy-4,4-tetramethylene-butanoic acid N-butyl-N-[2'-(1H-tetrazol-5-yl)biphenyl-4-ylmethyl]-amide;
2-carboxy-2-ethyl-butanoic acid N-butyl-N-[2'-(1H-tetrazol-5-yl)biphenyl-4-ylmethyl]-amide;
2-carboxy-2-ethyl-butanoic acid N-propyl-N-[2'-(1H-tetrazol-5-yl)biphenyl-4-ylmethyl]-amide;
2-carboxybutanoic acid N-propyl-N-[2'-(1H-tetrazol-5-yl)biphenyl-4-ylmethyl]-amide;
3-carboxy-3-ethyl-pentanoic acid N-butyl-N-[2'-(1H-tetrazol-5-yl)biphenyl-4-ylmethyl]-amide;
3-carboxy-3,3-pentamethylene-propanoic acid N-propyl-N-[2'-(1H-tetrazol-5-yl)biphenyl-4-ylmethyl]-amide;
3-carboxy-3,3-pentamethylene-propanoic acid N-butyl-N-[2'-(1H-tetrazol-5-yl)biphenyl-4-ylmethyl]-amide;
5-carboxy-5,5-tetramethylene-pentanoic acid N-propyl-N-[2'-(1H-tetrazol-5-yl)biphenyl-4-ylmethyl]-amide;
5-carboxy-5,5-tetramethylene-pentanoic acid N-butyl-N-[2'-(1H-tetrazol-5-yl)biphenyl-4-ylmethyl]-amide;
3-carboxy-2,2-tetramethylene-propanoic acid N-propyl-N-[2'-(1H-tetrazol-5-yl)biphenyl-4-ylmethyl]-amide;
3-carboxy-2,2-tetramethylene-propanoic acid N-butyl-N-[2'-(1H-tetrazol-5-yl)biphenyl-4-ylmethyl]-amide;
2,2-pentamethylene-2-trifluoromethanesulfonylamino-ethanoic acid N-butyl-N-[2'-(1H-tetrazol-5-yl)biphenyl-4-ylmethyl]-amide; and
2,2-pentamethylene-2-trifluoromethanesulfonylamino-ethanoic acid N-propyl-N-[2'-(1H-tetrazol-5-yl)biphenyl-4-ylmethyl]-amide or, in each case, a pharmaceutically acceptable salt thereof.

12. A compound selected from
4-carboxy-4,4-pentamethylene-butanoic acid N-propyl-N-[2'-(1H-tetrazol-5-yl)-biphenyl-4-ylmethyl]-amide;
4-carboxy-4,4-pentamethylene-butanoic acid N-butyl-N-[2'-(1H-tetrazol-5-yl)-biphenyl-4-ylmethyl]-amide;
N-propyl-N-[2'-(1H-tetrazol-5-yl)-biphenyl-4-ylmethyl]-isophthalic acid monoamide;
2-carboxy-phenylacetic acid N-butyl-N-[2'-(1H-tetrazol-5-yl)-biphenyl-4-ylmethyl]amide;
2-carboxy-phenylacetic acid N-butyl-N-[2'-(1H-tetrazol-5-yl)-biphenyl-4-ylmethyl]amide;
N-butyl-3-methyl-N-[2'-(1H-tetrazol-5-yl)biphenyl-4-ylmethyl]-2-(S)-trifluoromethane-sulfonylamino-butanoic acid amide; and
2-(S)-methanesulfonylamino-3-methyl-butanoic acid N-butyl-N-[2'-(1H-tetrazol-5-yl)biphenyl-4-ylmethyl]-amide; or, a pharmaceutically acceptable salt thereof.

13. A pharmaceutical composition comprising as active ingredient a compound according to claim 1, a pharmaceutically acceptable salt thereof, where appropriate together with conventional pharmaceutical excipients.

14. A method for the treatment of high blood pressure and cardiac insufficiency, comprising administering to a mammal in need of such treatment a therapeutically effective amount a compound according to claim 1, or a pharmaceutically acceptable salt thereof.

* * * * *